United States Patent
Loock et al.

(10) Patent No.: US 10,481,092 B2
(45) Date of Patent: Nov. 19, 2019

(54) MULTIPLEXED EXCITATION EMISSION MATRIX SPECTROSCOPY

(71) Applicant: QUEEN'S UNIVERSITY AT KINGSTON, Kingston (CA)

(72) Inventors: Hans-Peter Loock, Kingston (CA); Oliver Reich, Potsdam (DE); Nicholas L. P. Andrews, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 10 days.

(21) Appl. No.: 15/216,296

(22) Filed: Jul. 21, 2016

(65) Prior Publication Data
US 2017/0052118 A1   Feb. 23, 2017

Related U.S. Application Data

(60) Provisional application No. 62/194,919, filed on Jul. 21, 2015.

(51) Int. Cl.
*G01N 21/64* (2006.01)
*G01J 3/02* (2006.01)
(Continued)

(52) U.S. Cl.
CPC ........... *G01N 21/645* (2013.01); *G01J 3/021* (2013.01); *G01J 3/4406* (2013.01); *G01J 3/0218* (2013.01);
(Continued)

(58) Field of Classification Search
CPC ......... G01N 21/645; G01N 2021/6421; G01N 2021/6419; G01N 21/65; G01N 2201/0675; G01J 3/4406
See application file for complete search history.

(56) References Cited

U.S. PATENT DOCUMENTS 6,128,078 A    10/2000  Fateley
6,366,726 B1 * 4/2002  Wach ................... G01N 21/474
                                                         385/115
(Continued)

OTHER PUBLICATIONS

Zamkotsian, F.; Spano, P.; Bon, W.; Lanzoni, P.: Demonstrator of a Multi-Object Spectrograph based on the 2048x1080 DMD. In Emerging Digital Micromirror Device Based Systems and Applications Iv; Douglass, M. R., Oden, P. I., Eds., 2012; vol. 8254.
(Continued)

*Primary Examiner* — Michael P LaPage
(74) *Attorney, Agent, or Firm* — Stephen J. Scribner

(57) ABSTRACT

Described herein is an excitation emission matrix (EEM) spectrometer and method, comprising a multiplexer that encodes excitation light produced by at least one excitation light source; and a demultiplexer that decodes encoded light emitted from a sample, and produces an output indicative of a characteristic of the sample. Embodiments are described wherein the multiplexer and the demultiplexer may comprise FDM or OFDM, and wherein both the excitation light and the emitted light may be encoded using a DMA or a SLM. In some embodiments the same DMA or SLM may be used to encode the excitation light and the emitted light. In some embodiments excitation light may be encoded using a Walsh function, or the excitation light may be encoded using a Walsh function and the emitted light may be decoded using an inverse Hadamard transformation.

23 Claims, 20 Drawing Sheets

(51) Int. Cl.
  *G01J 3/44* (2006.01)
  *G01N 21/65* (2006.01)
  *G02B 6/36* (2006.01)
(52) U.S. Cl.
  CPC ..... *G01N 21/65* (2013.01); *G01N 2021/6419* (2013.01); *G01N 2021/6421* (2013.01); *G01N 2201/0675* (2013.01); *G02B 6/3624* (2013.01)

(56) References Cited

U.S. PATENT DOCUMENTS

| 6,996,292 | B1* | 2/2006 | Gentry | G01J 3/02 |
| | | | | 356/305 |
| 7,440,098 | B2 | 10/2008 | Christian et al. | |
| 7,719,680 | B2 | 5/2010 | Christian et al. | |
| 8,629,413 | B2* | 1/2014 | Betzig | G02B 21/0032 |
| | | | | 250/459.1 |
| 2008/0267248 | A1* | 10/2008 | Lee | G03F 7/7005 |
| | | | | 372/107 |
| 2009/0153752 | A1* | 6/2009 | Silverstein | G02B 27/1026 |
| | | | | 348/750 |
| 2010/0253935 | A1 | 10/2010 | Mackinnon et al. | |
| 2011/0133101 | A1* | 6/2011 | Viellerobe | A61B 1/00117 |
| | | | | 250/459.1 |
| 2012/0069342 | A1* | 3/2012 | Dalgleish | G01N 21/47 |
| | | | | 356/445 |
| 2014/0085420 | A1* | 3/2014 | Shahinian | A61B 1/045 |
| | | | | 348/45 |
| 2014/0268127 | A1* | 9/2014 | Day | G01J 3/0291 |
| | | | | 356/300 |
| 2015/0362713 | A1* | 12/2015 | Betzig | G02B 21/0064 |
| | | | | 250/459.1 |
| 2016/0202178 | A1* | 7/2016 | Acosta | G01N 21/27 |
| | | | | 356/303 |
| 2017/0176338 | A1* | 6/2017 | Wu | G01N 21/6458 |
| 2017/0343477 | A1* | 11/2017 | Santori | A61B 5/0071 |

OTHER PUBLICATIONS

Liu, J.; Shi, L.; Li, K.; Zheng, X. W.; Zeng, L. B.; Wu, Q. S.: A Two-Dimensional Double Dispersed Hadamard Transform Spectrometer. Spectroscopy and Spectral Analysis 2012, 32, 1722-1726.

Yan, P.; Hu, B. L.; Liu, X. B.; Sun, W.; Li, L. B.; Feng, Y. T.; Liu, Y. Z.: Hadamard Transform Spectrometer Mixed Pixels' Unmixing Method. Spectroscopy and Spectral Analysis 2011, 31, 2870-2873.

Liu, J.; Chen, F. F.; Liao, C. S.; Xw, Q.; Zeng, L B.; Wu, Q. S.: A Digital Micromirror Device-Based Hadamard Transform Near Infrared Spectrometer. Spectroscopy and Spectral Analysis 2011, 31, 2874-2878.

Quyen, N. T.; Jouan, M. D.; Dao, N. Q.; Da Silva, E; Al Phuong, D: New Raman spectrometer using a digital micromirror device and a photomultiplier tube detector for rapid on-line industrial analysis. Part II: Choice of analytical methods. Applied Spectroscopy 2008, 62, 279-284.

Quyen, N. T.; Da Silva, E.; Dao, N. Q.; Jouan, M. D: New Raman spectrometer using a digital micromirror device and a photomultiplier tube detector for rapid on-line industrial analysis. Part I: Description of the prototype and preliminary results. Applied Spectroscopy 2008, 62, 273-278.

McConnell, G.; Poland, S.; Girkin, J. M: Fast wavelength multiplexing of a white-light supercontinuum using a digital micromirror device for improved three-dimensional fluorescence microscopy. Review of Scientific Instruments 2006, 77.

Meyer, R. D.; Kerarney, K. J.; Ninkov, Z.; Cotton, C. T.; Hammond, P.; Statt, B. D.: Ritmos: a micromirror-based multi-object spectrometer. In Ground-Based Instrumentation for Astronomy, Pts 1-3; Moorwood, A. F. M., lye, M., Eds., 2004; vol. 5492; pp. 200-219.

Spudich, T. M.; Utz, C. K.; Kuntz, J. M.; Deverse, R. A.; Hammaker, R. M.; McCurdy, D. L.: Potential for using a digital micromirror device as a signal multiplexer in visible spectroscopy. Applied Spectroscopy 2003, 57, 733-736.

Dudley, D.; Duncan, W.; Slaughter, J: Emerging digital micromirroir device (DMD) applications. In Moems Display and Imaging Systems; Urey, H., Ed., 2003; vol. 4985; pp. 14-25.

Deverse, R. A.; Hammaker, R. M.; Fateley, W. G.: An improved Hadamard encoding mask for multiplexed Raman imaging using single channel detection. Journal of Molecular Structure 2000, 521, 77-88.

Deverse, R. A.; Hammaker, R. M.; Fateley, W. G.: Realization of the Hadamard multiplex advantage using a programmable optical mask in a dispersive flat-field near-infrared spectrometer. Applied Spectroscopy 2000, 54, 1751-1758.

Deverse, R. A.; Hammaker, R. M.; Fateley, W. G.; Graham, J. A.; Tate, J. D.: Spectrometry and imaging using a digital micromirror array. American Laboratory 1998, 30, 112S-+.

Omrani, H. et al., "Fluorescence excitation-emission matrix (EEM) spectroscopy and cavity ring-down (CRD) absorption spectroscopy of oil-contaminated jet fuel using fiber-optic probes", Analyst, 2012, 137, pp. 2782-2790.

Ma, J., et al., "Easily fabricated, robust fiber-optic probe for weak fluorescence detection: modeling and initial experimental evaluation", Optics Express, 2012, 20, pp. 4805-4811.

Omrani, H.; Dudelzak, A. E.; Hollebone, B. R; Loock, H.-P.: Assessment of the oxidative stability of lubricant oil using fiber-coupled fluorescence excitation-emission matrix spectroscopy. Analytica Chimica Acta 2004, 811, 1.

Andrews, N. L. P.; Fan, J. Z.; Omrani, H.; Dudelzak, A. E; Loock, H.-P.: Comparison of lubricant oil antioxidant analysis by fluorescence spectroscopy and linear sweep voltammetry. Tribology International 2016, 94, 279-287.

Andrews, N. L. P.; Fan, J. Z.; Forward, R. L.; Chen, M. C.; H.-P. Loock.: Determination of the thermal, oxidative and photochemical degradation rates of scintillator liquid by fluorescence EEM spectroscopy. Physical Chemistry Chemical Physics 2017, 19 (1), 73-81.

Gouzman, M.; Lifshitz, N.; Luryi, S.; Semyonov, O.; Gavrilov, D.; Kuzminiskiy, V.: Excitation-emission fluorimeter based on linear interference filters. Applied Optics 2004, 43, 3066.

Hart, S. J.; Jiji, R. e. D.: Light emitting diode excitation emission matrix fluorescence spectroscopy. The Analyst 2002, 127, 1693-1699.

Muroski, A. R.; Booksh, K. S.; Myrick, M. L: Single-measurement excitation / emission matrix spectrofluorometer for determination of hydrocarbons in ocean Water. 1. Instrumentation and background correction. Analytical Chemistry 1996, 68, 3534-3538.

Adams, M. L.; Enzelberger, M.; Quake, S.; Scherer, A.: Microfluidic integration on detector arrays for absorption and fluorescence microspectrometers. Sensors and Actuators A-Physical 2003, 104, 25.

Motz, J. T.; Yelin, D.; Vakoc, B, J.; Bouma, B. E.; Terarney, G. J: Spectral- and frequency-encoded fluorescence imaging. Optics Letters 2005, 30, 2760.

Yuan, J.; Peng, L.; Bouma, B. E.; Tearney, G. J: Quantitative FRET measurement by high-speed fluorescence excitation and emission spectrometer. Optics Express 2010, 18, 18839.

Peng, L.; Gardecki, J. A.; Bouma, B. E.; Tearney, G. J.: Fourier fluorescence spectrometer for excitation emission matrix measurement. Optics Express 2008, 16, 10493.

Heintzmann, R.; Lidke, K. A.; Jovin, T. M.: Double-pass Fourier transform imaging spectroscopy. Optics Express 2004, 12, 753.

Kidder, L. H.; Levin, I. W.; Lewis, E. N.; Kleinman, V. D.; Heilweil, E. J.: Mercury cadmium telluride focal-plane array detection for mid-infrared Fourier-transform spectroscopic imaging. Optics Letters 1997, 22, 742.

Lewis, E. N.; Treado, P. J.; Reeder, R. C.; Story, G. M.; Dowrey, A. E.; Marcott, C.; Levin, I.W.: Fourier transform spectroscopic imaging using an infrared focal-plane array detector. Analytical Chemistry 1995, 67, 3377.

Da Silva, H.E.B., et al., "Dual-Beam Near-Infrared Hadamard Spectrophotometer", Applied Spectorscopy, vol. 55, No. 6, pp. 715-721, (2001).

(56) References Cited

OTHER PUBLICATIONS

Deverse, R.A. et al., "Hadarnard transform Raman imagery with a digital micro-mirror array", Vibrational Spectroscopy, vol. 19, pp. 177-186, (1999).

Deverse, R.A., et al., "Realization of the Hadarmard Multiplex Advantage Using a Programmable Optical Mask in a Dispersive Flat-Field Near-Infrared Spectrometer", Applied Spectroscopy, vol. 54, No. 12, pp. 1751-1758, (2000).

Deverse, R.A., et al., "An improved Hadamard encoding mask for multiplexed Raman imaging using single channel detection", Journal of Molecular Structure, vol. 521, pp. 77-88, (2000).

Fateley, W.G., et al., "Modulations used to transmit information in spectrometry and imaging", Journal of Molecular Structure, vol. 550-551, pp. 117-122, (2000).

Fateley, W.G., et al., "The other spectroscopy: demonstration of new de-dispersion imaging spectrograph", Vibrational Spectroscopy, vol. 29, pp. 163-170, (2002).

Hammaker, R.M. et al., "Multi-dimenstional Haramard transform spectrometry", Journal of Molecular Structure, vol. 348, pp. 135-138, (1995).

Plankey, F.W., et al., "Hadamard Spectrometer for Ultraviolet-Visible Spectrometry", Analytical Chemistry, vol. 46, No. 8, pp. 1000-1005, (1974).

Smith, M.W., "Theoretical description and numerical simulations of a simplified Hadamard transform imaging spectrometer", imaging Spectrometry VIII, Proc. of SPIE, vol. 4816, pp. 372-380, (2002).

Streeter. L. et al., "Visible/near infrared hyperspectral imaging via spatial illumination source modulation", J. Near Infrared Spectroscopy, vol. 15, pp 395-399, (2007).

Sun, X. et al., "An engineering prototype of Hadamard transform spectral imager based on Digital Micro-mirror Device", Optics and Laser Technology. vol. 44, pp. 210-217, (2012).

Wang, W., et al., "Realization of Hadarmard Transform Encoding Mask Using Programmable Digital Micro-mirror Device". Key Engineering Materials, vol. 483, pp. 497-502, (2011).

Wehlburg, C.M., "Optimization and Characterization of an Imaging Hadamard Spectrometer", Algorithms for Multispectral, Hyperspectral, and Ultraspectral Imagery VII, Proc. SPIE, vol. 4381, pp. 506-515, (2001).

Xu, J, et al., "Analysis and study of the interlaced encoding pixels in Hadamard transform spectral imager based on DMD", Optics arid Lasers in Engineering, vol. 50, pp. 458-464, (2012).

\* cited by examiner

MULTIPLEXED EXCITATION EMISSION MATRIX SPECTROSCOPY

RELATED APPLICATIONS

This application claims the benefit of the filing date of U.S. patent application Ser. No. 62/194,919, filed on Jul. 21, 2015, the contents of which are incorporated herein by reference in their entirety.

FIELD

This invention relates generally to the field of spectroscopy. More specifically, this invention relates to excitation emission matrix (EEM) spectroscopy.

BACKGROUND

Fluorescence spectroscopy is a highly sensitive, nearly background-free technique for chemical detection. Fluorescence detection is typically achieved by either single-line UV excitation and dispersion of the entire fluorescence emission spectrum (e.g., laser induced fluorescence (LIF)) or by tuning the excitation source over a wide wavelength range and detecting the entire spectrum of emitted light as a function of excitation wavelength with a broad band detector (e.g., excitation spectroscopy). In liquid samples excitation and emission bands are broad, making it difficult to identify an analyte. Excitation emission matrix (EEM) spectroscopy (EEMS) combines both techniques. The excitation wavelength is scanned and an EEM is produced by recording a fluorescence emission spectrum at each of the many excitation wavelengths. The EEM is used to generate a three-dimensional spectrum (resembling a "topographical map") that allows analytes to be distinguished in a sample of a mixture by separating broad fluorescent features into key dominant spectroscopic components that may correspond to the individual fluorophores, in some cases.

Determining the concentration of specific fluorophores within a mixture can prove complicated, especially when the broad fluorescence peaks overlap. This problem can be solved using multivariate data analysis, such as principle component analysis (PCA) or parallel factor analysis (PARAFAC). Through such analyses the excitation emission matrix spectra can be decomposed into its various components and hence number of fluorophores, a feat which would be otherwise difficult for complicated mixtures.

Currently, fluorescence EEMS is typically carried out using a spectrometer that scans a pivoting grating (or other light dispersing element) so that only a small wavelength ranges passes through a slit to excite the sample. At each of the excitation wavelengths the spectrometer collects the fluorescence onto a second pivoting grating and slit to direct a selected emission wavelength to a broad band photodetector, such as an avalanche photodiode or photomultiplier. In an alternative spectrometer the second slit and photodetector are replaced with an array detector for higher data acquisition rates. Since array detectors tend to be less sensitive than broad-band photodetectors the latter is less efficient as it could be. Both designs require at least one grating that is mechanically moved. This is a time-consuming process that uses only a fraction of the light to generate the EEM spectrum (e.g., about 1/10,000 for the former and 1/100 for the latter design, depending on the required spectral resolution and spectral range) of the light to generate the EEM spectrum.

A solution to this problem is to utilise a variant of wavelength division multiplexing. If each excitation wavelength is individually modulated with a unique frequency, the entire spectrum of the light source can be used to excite the sample and all the emission collected simultaneously. The spectrum can then be obtained through demodulation of the resultant signal, for example by using a Fourier transform. However, Fourier transforms require analogue or high-bit digital modulation of light intensities and thus can be afflicted with harmonics that interfere with one another and confound the results.

SUMMARY

One aspect of the invention relates to an EEM spectrometer, comprising: at least one excitation light source; a multiplexer that encodes excitation light produced by the at least one excitation source; a conduit that conducts encoded excitation t to a sample; a conduit that conducts encoded emitted light from the sample; a detector that detects the encoded emitted light; a demultiplexer that decodes the encoded emitted light and produces an output signal; and, optionally a display device that that displays the output signal.

In various embodiments, the multiplexer and the demultiplexer comprise frequency division multiplexing (FDM) or orthogonal frequency division multiplexing (OFDM). In one embodiment, both the excitation light and the emitted light are encoded using a spatial light modulator (SLM) or a digital micromirror array (DMA). Embodiments may comprise recording (e.g., with a photodiode or photomultiplier tube, PMT) and subsequently decoding the emitted light signal. In one embodiment the same DMA or SLM may be used to encode the excitation light and the emitted light. In one embodiment the excitation light may be encoded by a DMA or SLM and the emitted light may be recorded by a photoarray detector.

In one embodiment the excitation light is encoded using a Walsh function. In another embodiment the excitation encoded using a Walsh function and the emitted light is decoded using an inverse Hadamard transformation.

In one embodiment the conduit that directs encoded excitation light to the sample and the conduit that directs encoded emitted light from the sample may comprise a bifurcated fibre probe. In one embodiment the bifurcated fibre probe comprises: an excitation end from which a first set of optical fibres receives excitation light; an emission end from which a second set of optical fibres emit emitted light; and a probe end from which the excitation light is outputted from the first set of optical fibres and the emitted light is received from a sample by the second set of optical fibres; wherein the first set of optical fibres at the excitation end are arranged in a rectangular pattern; and wherein the probe comprises a beveled window that reduces back reflections.

Another aspect of the invention relates to a bifurcated fibre probe, comprising: an excitation end from which a first set of optical fibres receives excitation light; an emission end from which a second set of optical fibres emit emitted light; and a probe end from which the excitation light is outputted from the first set of optical fibres and the emitted light is received from a sample by the second set of optical fibres; wherein the first set of optical fibres at the excitation end are arranged in a rectangular pattern; and wherein the probe comprises a bevelled window that reduces back reflections.

Another aspect of the invention relates to an EEM spectroscopy method, comprising: using a multiplexer to encode excitation light produced by at least one excitation light source; conducting the encoded excitation light to a sample; conducting encoded emitted light from the sample; detecting the encoded emitted light and using a demultiplexer to decode the encoded emitted light and produce an output signal; and, optionally displaying the output signal.

The method may comprise multiplexing and demultiplexing using FDM or OFDM. The method may comprise encoding the excitation light using a DMA or SLM. The method may comprise encoding the excitation light and decoding the emitted light using the same DMA or SLM. The method may comprise encoding the excitation light using a DMA or SLM and recording the emitted light using a photoarray detector. The method may comprise encoding the excitation light using Walsh functions. The method may comprise encoding the excitation light using Walsh functions and decoding the emitted light using an inverse Hadamard transformation.

Another aspect of the invention relates to optical components that couple the excitation light to the multiplexer. In one embodiment such optical components include a fibre bundle having a first end that is circular (e.g., substantially circular as may be determined by the arrangement of fibres within the bundle) and a second end that is in the form of a slit (e.g., as may be determined by the arrangement of the fibres in one or more rows). The circular end receives excitation light which is directed through the fibre bundle and the slit to the multiplexer, wherein the amount of light reaching dispersive optics of the multiplexer is maximized while maintaining a good dispersive resolution. In one embodiment, a further element is disposed after the second end to focus dispersed light on a multiplexer component, such as a DMA. In one embodiment the further element may comprise a translation stage.

Another aspect of the invention relates to triggering of the DMA and detector. In one embodiment, the DMA or SLM sends a trigger signal after the minors have been turned on (or off) to control timing of data acquisition by the detector. For example, the DMA or SLM may send a trigger pulse after the mirrors have been turned on so that the detector may record a signal for each encoded Hadamard mask. Such triggering allows embodiments to be run automatically, or with minimal user input, and without cross talk between consecutive spectra. In another embodiment, the detector may be used as a master clock and trigger the DMA or SLM to turn the mirrors on (or off).

Embodiments described herein may be applied to all spectroscopy techniques in which a sample modifies the spectrum of incident light to produce a spectrum of emitted light. Such techniques include, but are not limited to, Raman scattering, Rayleigh and Mie scattering, thin film reflection and interferometry, phosphorescence as well as variants of these methods such as surface enhanced Raman scattering, tip enhanced Raman scattering, localised surface plasmon resonance spectroscopy, and others.

BRIEF DESCRIPTION OF THE DRAWINGS

For a greater understanding of the invention, and to show more clearly how it may be carried into effect, embodiments will be described, by way of example, with reference to the accompanying drawings, wherein:

FIG. 8B, 256 pictures) according to an embodiment described herein, and using a Varian Cary Eclipse spectrometer (FIG. 8C);

DETAILED DESCRIPTION OF EMBODIMENTS

Figure 1:
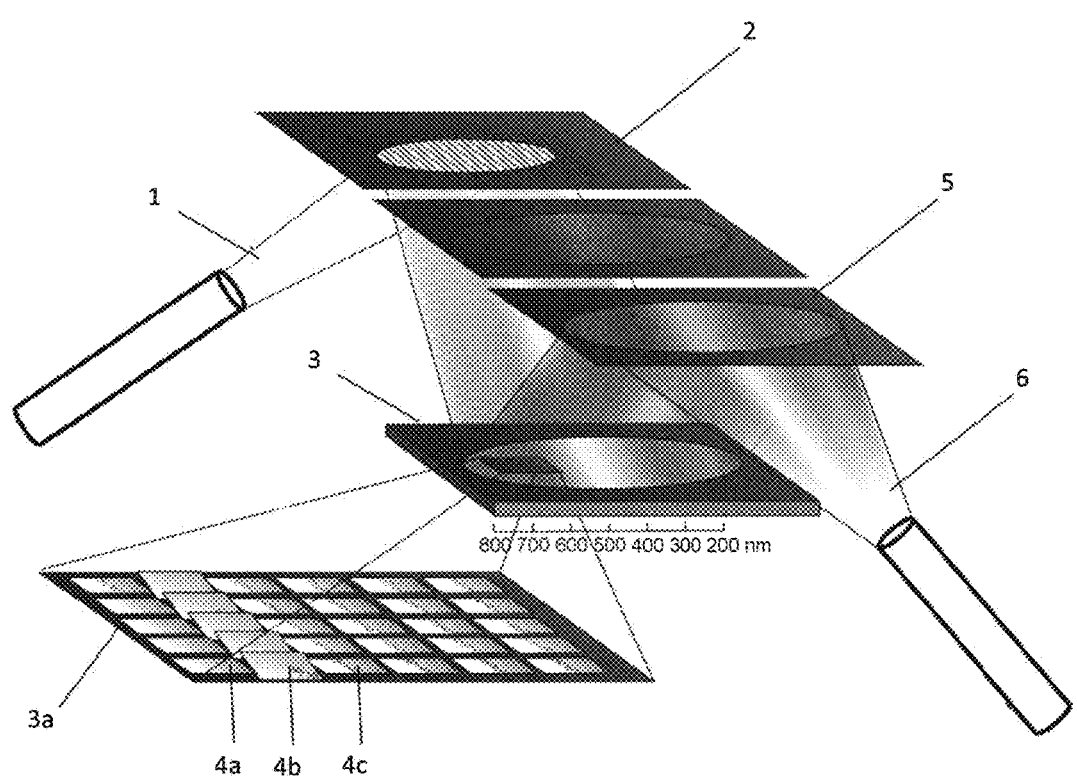
FIG. 1 is a schematic diagram of a spectrometer according to an embodiment described herein.

The challenges presented by multiplexing in absorption spectroscopy and in emission (e.g., fluorescence or Raman) spectroscopy are usually moved to the detection side. For example, the broad spectrum transmitted (for absorption) or emitted (for fluorescence or Raman from the sample is typically directed to a dispersion element such as a grating or prism. The output from the grating can then be directed either towards an array (imaging) detector or through a scanning grating and slit to a broad band detector. Depending on the light intensity an array detector is able to collect an entire spectrum in less than a second without any moving parts, whereas a scanning gating may require from seconds to minutes to acquire a spectrum depending on the required spectral resolution, the efficiency of the detector, and the light intensity. When collecting fluorescence EEM spectra one can scan either the excitation wavelength and record the fluorescence spectrum using an array detector, or one can scan both wavelengths using two tuneable gratings. Compared to a point-by-point scanning instrument, using an array detector would present an increase in acquisition rate by one or two orders of magnitude.

Fluorescence EEM spectroscopy using a two-dimensional array detector is also possible. The excitation light may be spatially dispersed and a sample illuminated with a "rainbow" of colours. For each of the excitation colours the fluorescence spectrum can then be obtained on a large grating and projected onto a broad band 2D photo detector such as that of a CCD or CMOS chip. If the excitation light is dispersed along one spatial axis of the 2D photodetector and the emission light is dispersed along the second axis of this detector, the resulting image is identical to the EEM spectrum. This technique works for large, homogeneous static samples with low scattering and provides a fair spectral resolution. However, there is considerable cross talk between channels, and the method cannot easily be fibre-coupled.

In some embodiments, digital (e.g., 2-bit) modulation tags are employed to identify the wavelengths. Here, each wavelength is modulated with a specific pseudo-random sequence of 1's and 0's, and the signal from the photodetector is demodulated using the known pseudo-random codes.

In the simplest approach separate individual light sources, such as lasers or light emitting diodes (LEDs) are modulated—each with a different on-off sequence. In another approach to such digital encoding either a spatial light modulator (SLM) or a digital micromirror array (DMA), also referred to as a digital micromirror device (DMD), may be used. An SLM is a switchable filter array, typically based on the modulation of liquid crystals that permits a spatially resolved modulation of light intensities. A DMA is an array of hinge-mounted microscopic mirrors, each mirror able to be individually switched between "on" and "off" states as determined by the position of the mirror. A DMA is typically fabricated on a semiconductor substrate (e.g., complementary metal oxide semiconductor, CMOS) memory layer. For each mirror, a voltage can be applied to the memory layer. After a trigger signal, the mirror is then free to rotate through electrostatic attraction between the mirror and memory cell.

While digital encoding using separate light sources is straightforward, a grating is required to modulate wavelengths independently using a SLM or a DMA. As to digital encoding, briefly, the rainbow from the fixed dispersion elements is projected onto a SLM or DMA such that each column is irradiated with a different colour and the same row elements in each column are exposed to the same colour. For example, in a DMA the mirrors in each column of the array (corresponding to a single colour) direct the light either to a beam dump or to a second grating that serves to combine the colours into a beam of "encoded" white light.

As used herein, the term "rainbow" is intended to mean a portion of the electromagnetic spectrum comprising two or more colours of light.

As used herein, the term "colour" is intended to mean a portion of the electromagnetic spectrum whose width is defined, for example, by the spectral bandwidth of one or more light sources, or by the spectral bandwidth associated with a column of micromirrors in a DMA, or the spectral bandwidth of a selected element of a SLM.

In one example, shown schematically in FIG. 1, white light 1 is directed onto a dispersion grating 2, which reflects the spectrum of the white light source onto a DMA 3. A portion of the DMA is shown enlarged at 3a. Columns of micromirrors 4a, 4b, 4c, etc., then are switched according to an encoding pattern to direct specific wavelengths towards a second grating 5, which recombines the colours to create an encoded white light spectrum 6. This encoded light may be directed to a sample to perform absorption/transmission spectroscopy or scattering spectroscopy. In various embodiments the encoded light is directed to the sample, and/or reflected light is directed from the sample, via a conduit that may comprise one or more optical components including, but not limited to, a waveguide, at least one fibre, a mirror, and a prism.

In order to perform EEM spectroscopy the encoded light is directed towards a sample and its emission is detected. Three different detection schemes may be implemented. For example, a DMA may be used to encode the white light for excitation of the sample and a fluorescence spectrometer consisting of a fixed grating and array detector may be used to record the dispersed fluorescence spectra for each of the encoding patterns. Alternatively, a second grating and DMA (e.g., as shown in FIG. 1) may be used on the fluorescence emission side of the EEM spectrometer to encode the emission colours analogous to the excitation colours for detection in a single broad band detector. Two of such multiplexing units are used. One is used to encode the excitation light and the second unit encodes the fluorescence. Each pixel in the EEM spectrum is therefore doubly encoded. For simplification, passive optical components (e.g., lenses) are omitted in this description. Finally, the same DMA may be used for encoding both the excitation light and the fluorescence emission. In this case the excitation light and emission light may be directed towards a different region on the same DMA.

Digital micromirror arrays have been proposed previously for use as a tuneable slit in fluorescence spectroscopy, and in emission spectroscopy using frequency encoding together with a FT transform. However, this is the first report of a DMA used for EEM spectroscopy, and the first report of using a multiplexing scheme together with a detector for high-sensitivity and rapid acquisition of 2D spectra.

Fluorescence and phosphorescence lifetime measurements may be made with the same setup as long as the intensity decay of the fluorescence signal is time-resolvable for each of the excitation-emission wavelength pairs, i.e., for each "pixel" in the EEM image. If the excitation wavelength is encoded using a modulation scheme, as described above, the lifetime measurement may be made at each of the fluorescence wavelengths and then correlated to the excitation wavelengths using the same inverse transformation.

Embodiments described herein employ a Hadamard transform (HT) instead of a Fourier transform, and thus overcome the drawbacks associated with sine functions.

The Hadamard transform (HT) is a binary equivalent of the analogue Fourier transform (FT). Instead of using sine functions as in FTs, the HT uses a set of Walsh functions, which are binary with values 1 and −1. The Walsh functions are mutually orthogonal and the Hadamard matrix is constructed as a square symmetric matrix from rows and columns of Walsh functions. The HT involves multiplying a signal (dimension of $2^m$) with the Hadamard matrix $H_m$, where m is the number of bits. The elements of the Hadamard matrix may be obtained from $$(H_m)_{i,j} = \frac{1}{2^{m/2}}(-1)^{i,j} \quad (1)$$

where i and j represent the indices within the Hadamard matrix and i,j represents the binary dot product of i and j. For example, a 2-bit Hadamard matrix $H_2$, is:

$$H_2 = \frac{1}{2}\begin{pmatrix} 1 & 1 & 1 & 1 \\ 1 & -1 & 1 & -1 \\ 1 & 1 & -1 & -1 \\ 1 & -1 & -1 & 1 \end{pmatrix} \quad (2)$$

The orthogonality of the Walsh functions implies that $H^2=I$ and the intensities (or spectra) recorded at differing wavelengths (or times) will not affect one another; unlike the effects of harmonics in FTs. For a binary Hadamard transform as applied to the "on" and "off" states of the mirrors in a DMA, the values of −1 are replaced with zeros $$H_2 = \begin{pmatrix} 1 & 1 & 1 & 1 \\ 1 & 0 & 1 & 0 \\ 1 & 1 & 0 & 0 \\ 1 & 0 & 0 & 1 \end{pmatrix} \quad (3)$$

Computers are able to decode HT encoded signals much faster than their FT equivalents and decoding can frequently be done in real-time.

According to embodiments described herein, the Hadamard mask may be applied to the wavelength spectrum of the excitation light source using a DMA. However, other configurations will be apparent to those of ordinary skill in the art.

One embodiment provides EEMS based on modulating the intensity of each excitation wavelength and, independently and separately, of each emission wavelength, using two different Hadamard masks. Each excitation-emission wavelength pair is therefore encoded by a product of two Walsh functions. A photodetector records a superposition of all the frequency-encoded light signals, and a fast algorithm then de-multiplexes the signal into the wavelength pairs. By knowing the specific modulation frequency assigned to every wavelength pair the detected signal is demodulated to produce the Whole EEM spectrum. This embodiment requires either separately modulated light sources such as lasers or LEDs or a DMA (or SLM) combined with a grating to encode the excitation wavelengths as well as a second DMA (or SLM) and grating to encode the emission wavelengths. In an alternative embodiment, the emission light is passed through the same grating and onto the same DMA (or SLM) but strikes a differently encoded section of the DMA (or SLM) to encode the emission light.

In another embodiment, the excitation light is encoded with a Hadamard mask using a DMA (or SLM) and dispersion grating, and all emission wavelengths are collected in an array spectrometer. This embodiment simplifies the optical alignment and reduces the cost, since currently a DMA is more expensive than a spectrometer. This embodiment also increases the optical throughput by a factor of two, since with each pass over a DMA, one-half of the wavelengths have to be rejected.

Embodiments described herein have applications in fields such as, but not limited to, X-ray, ultraviolet, visible, near-infrared, infrared, and terahertz spectroscopy.

Embodiments will be further described by way of the following non-limiting Examples.

EXAMPLE 1

DMA Hadamard EEM Spectrometer

Figure 2:
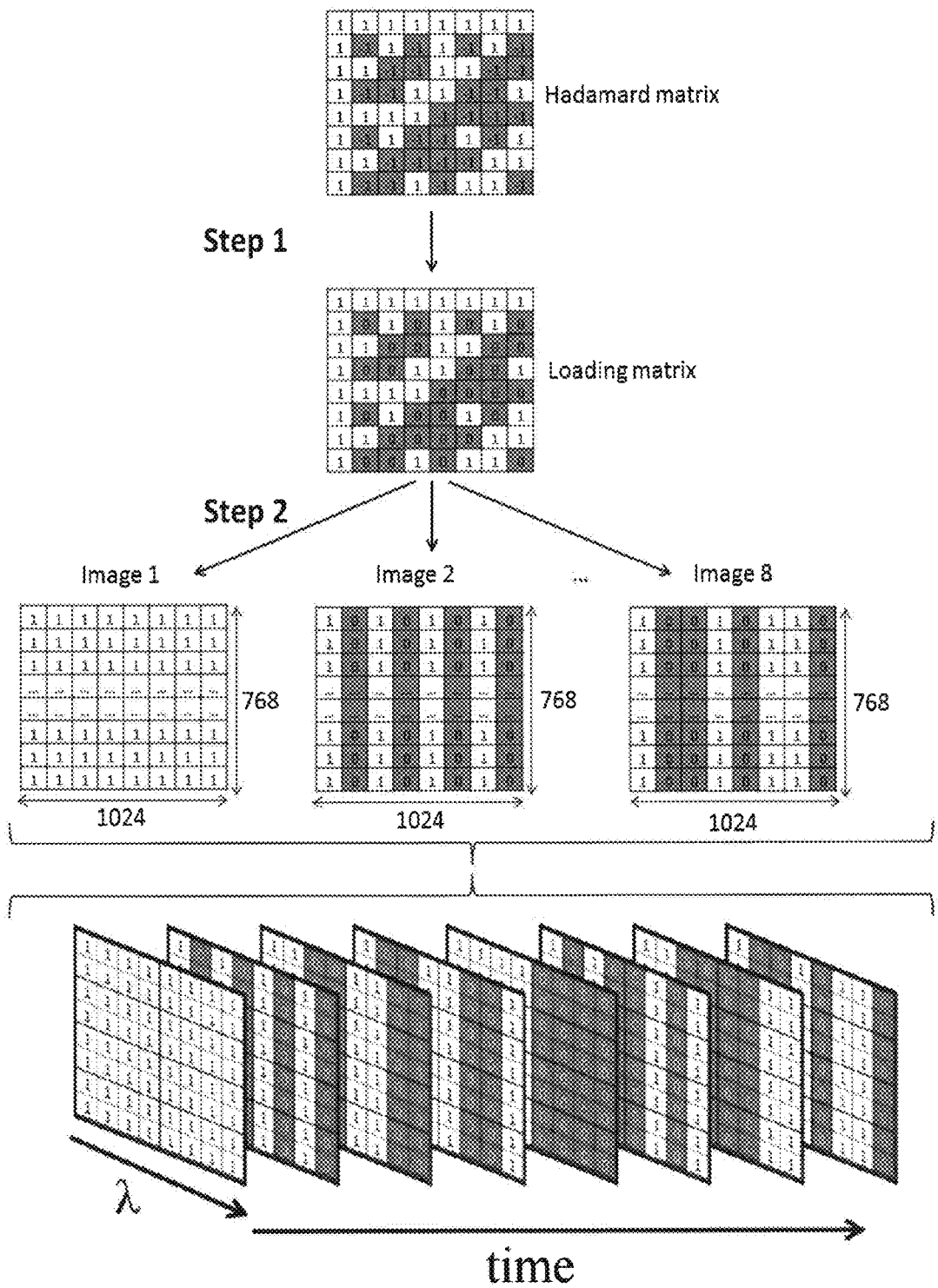
FIG. 2 is a schematic representation of a method of generating a Hadamard mask, wherein m=3, according to one embodiment.

In this example a compact spectrometer (USB2000+, Ocean Optics, Inc., Florida, USA) was reconfigured. In its original configuration the spectrometer collimates the light from a multimode optical fibre onto a one-dimensional (1D) CCD array at high resolution using a reflection gating and a series of optical elements. The CCD array was removed and replaced with a DMA (ViALUX Chemnitz, Germany, V4100 XGA UV module, 1024×768 micromirrors, 13.6 μm pitch based on Texas Instruments DLP technology) to encode the excitation light. The Hadamard mask was generated and displayed on the DMA using custom designed MATLAB® (The MathWorks, Inc., Natick, Mass., USA) codes. The Hadamard mask was generated using a Hadamard matrix of order $2^m$ as shown in FIG. 2 where, for illustration purposes, m=3 and the DMA micromirrors are grouped into 8 segments. With the available DMA the Hadamard matrix may be scaled up to 1024×1024 (m=10). At this resolution each DMA column may be coded individually.

Referring to FIG. 2, in Step 1, since the DMA can only encode binary images in which mirrors can only assume two stable positions, for all Walsh functions (except for the unity function) one-half of the light is directed into a beam dump (i.e., the "rejected" light). However, if a second detector is used to collect the rejected light, a parallel measurement of, e.g., a reference or calibration sample, may be made. In Step 2, each row in the loading matrix generates a mask that is displayed onto the DMA as an image. The columns are spread along the 1024 pixels, while all the rows have the same value. As the columns on the DMA represent a different wavelength alight, only the "on" (+1) values are detected for each image, creating a mask.

Figure 3:
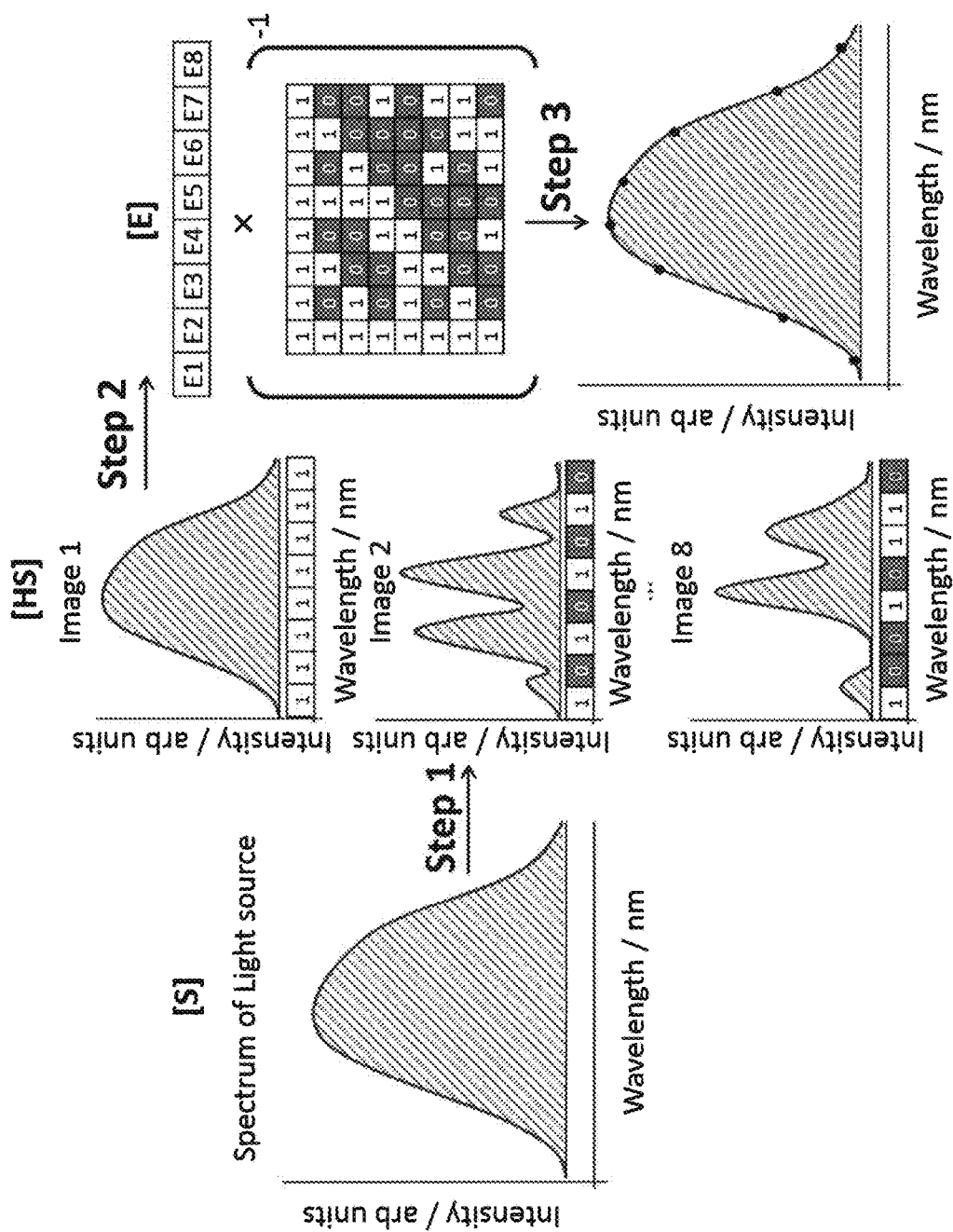
FIG. 3 is a schematic representation of modulation and demodulation of a light source using a Hadamard mask, according to one embodiment.

FIG. 3 shows how the emission profile of the light source may be modulated and demodulated using the DMA. The Hadamard masks are displayed sequentially as separate images on the DMA (FIG. 2), Each image produces a unique combination of excitation wavelengths. After irradiation of the sample a corresponding emission (or absorption or transmission or scattering) spectrum is produced whose contributions arise only from those wavelengths that strike the DMA where the mirrors are on (+1) and not where the mirrors are off (0). To obtain the emission spectrum of the light source S from the modulated data HS, each spectrum from an image on the DMA is collected (Step 1), and then integrated and placed into an array E, where the index of the array corresponds to the image/spectrum number (Step 2). At Step 3 the spectrum of the light source is obtained by multiplying E with the inverse of the binary Hadamard matrix H (Equation 3). For example, to encode the emission spectrum of a light source—here represented as rows in a matrix S where all rows are identical—each wavelength is modulated separately by an individual row of the Hadamard matrix. The resulting sequence of spectra is represented by the Hadamard product giving matrix HS in which each row represents a spectrum $$[H] \cdot [S] = [HS] \quad (4)$$

$$[H_{ij}] \cdot \begin{bmatrix} S_{11} & S_{12} & \ldots & S_{1j} \\ \vdots & & & \vdots \\ S_{j1} & S_{j2} & \ldots & S_{jj} \end{bmatrix} = \begin{bmatrix} H_{11}S_1 & H_{12}S_2 & \ldots & H_{1j}S_j \\ \vdots & & & \vdots \\ H_{i1}S_{j1} & \ldots & \ldots & H_{ij}S_{jj} \end{bmatrix}$$

If only the integrated intensity of each spectrum is measured, then the intensity for each mirror configuration can be represented by the column vector:

$$[E] = \begin{bmatrix} \sum_{k=1}^{j} H_{1k}S_k \\ \vdots \\ \sum_{k=1}^{j} H_{ik}S_k \end{bmatrix} = H_{ij} \times \begin{bmatrix} S_1 \\ \vdots \\ S_j \end{bmatrix} \quad (5)$$

The spectrum of the light source, $(S_1 \ldots S_j)$, can be obtained by multiplying E with the inverse of the binary Hadamard matrix $$\begin{bmatrix} S_1 \\ \vdots \\ S_j \end{bmatrix} = H_{ij}^{-1} \times \begin{bmatrix} \sum_{k=1}^{j} H_{i,k}S_k \\ \vdots \\ \sum_{k=1}^{j} H_{ik}S_k \end{bmatrix} \quad (6)$$

Encoding and decoding of the light source spectrum may be useful when recording reflection, transmission or absorption spectra.

When the encoded excitation light HS is used to excite fluorescence in a sample, the resulting fluorescence matrix F is given by:

$$\begin{bmatrix} H_{11}S_1 & H_{12}S_2 & \ldots & H_{1j}S_j \\ \vdots & & & \vdots \\ H_{i1}S_1 & \ldots & \ldots & H_{ij}S_j \end{bmatrix} \times M_{ij} = \begin{bmatrix} f_{11} & f_{12} & \ldots & f_{1j} \\ \vdots & & & \vdots \\ f_{i1} & \ldots & \ldots & f_{ij} \end{bmatrix} \quad (7)$$

$$[HS][M] = [F]$$

where $M_{ij}$ is the fluorescence intensity at the wavelength j with normalized excitation at wavelength i, i.e., the desired EEM spectrum. Each row of matrix F represents the fluorescence spectrum for a given mirror configuration. To demodulate F into the EEM spectrum $[M]^T$, the transpose of [F], i.e., $[F]^T$, is multiplied with the transpose inverse of the source weighted Hadamard matrix $[[HS]^{-1}]^T$ $$[M]^T = [F]^T [[HS]^{-1}]^T \quad (8)$$

A program may be written to generate Hadamard matrices using equation (1), and to decode the fluorescence signal [F] thereby generating the EEM spectrum [M] according to equation (8).

Figure 4:
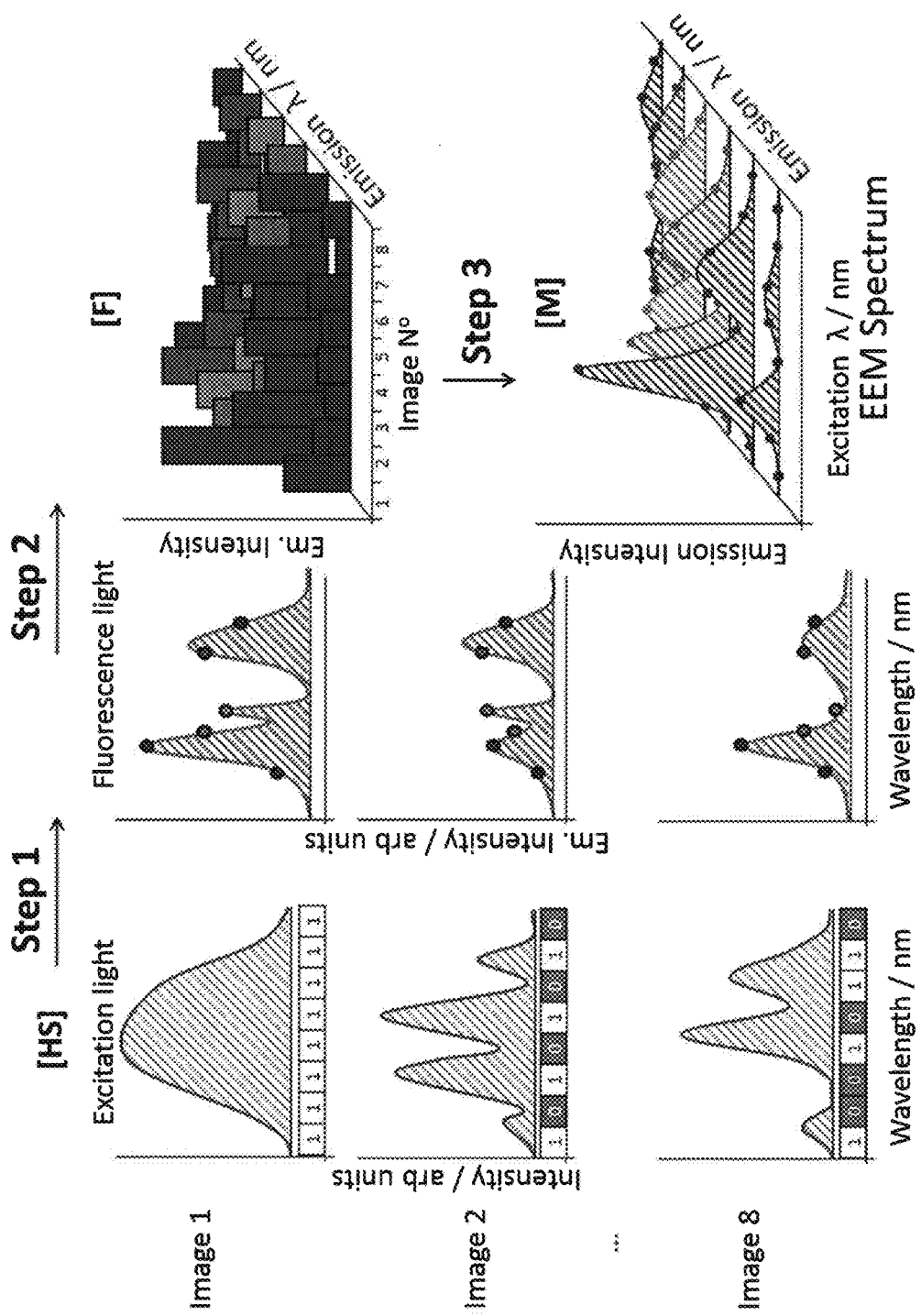
FIG. 4 is a schematic representation of generation of an EEM spectrum through Hadamard modulation, according to one embodiment.

FIG. 4 shows how an EEM spectrum M may be produced using the Hadamard transform technique. Each Hadamard mask displayed by the DMA generates a modulated excitation spectrum HS which, at Step 1, produces a characteristic fluorescence spectrum after interaction with a fluorescing sample. At Step 2 these fluorescence spectra are collected into a 3D array of spectral data F which contains the fluorescence intensities as a function of Hadamard mask index and emission wavelength. At Step 3, to demodulate F into an EEM spectrum M, the Hadamard index is converted to excitation wavelength through multiplication of the transpose of F, with the transpose inverse of the weighted Hadamard matrix $[[HS]^{-1}]^T$ (equation (8)). This operation may be executed using MATLAB or other suitable software so that the EEM spectrum can be generated from the modulated fluorescence rapidly; e.g., typically within 15 s or less for a 6-bit matrix and non-optimized code.

Figure 5A:
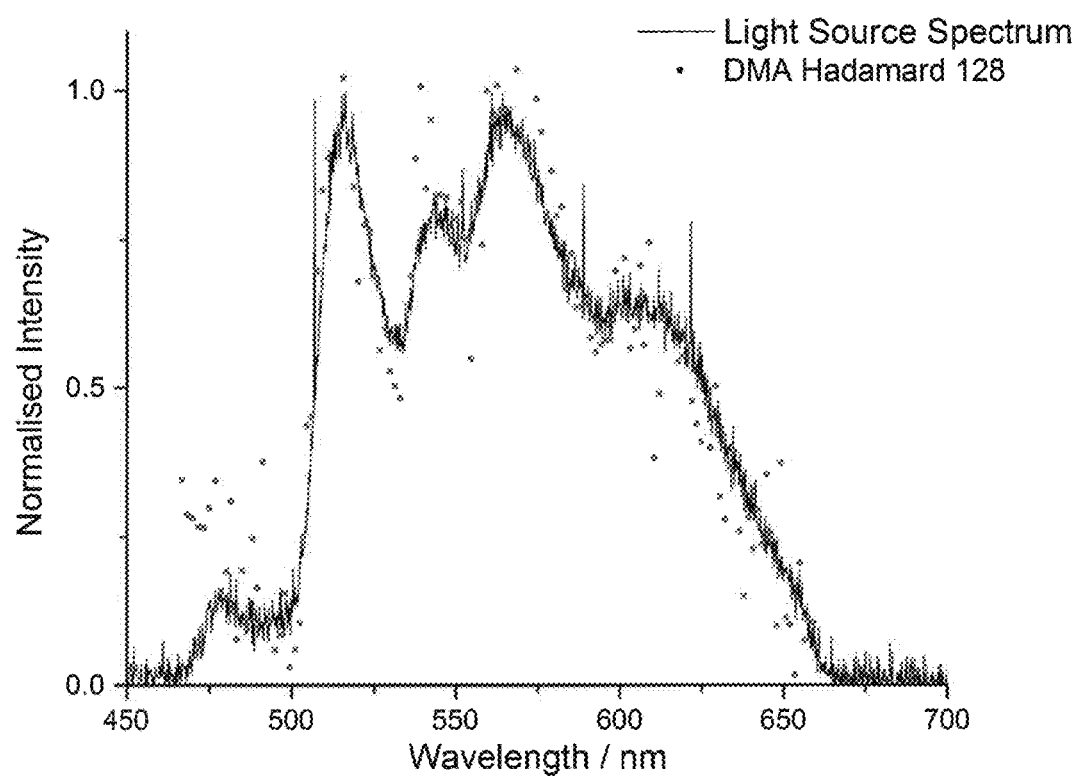
FIGS. 5A and 5B are plots showing experimental results, wherein the lines in FIG. 5A represent the spectrum of a tungsten lamp light source without modulation, and the dots represent modulated and demodulated data points for a Hadamard mask (m=7) having 128 elements, and wherein the lines in FIG. 5B represent the spectrum of a light emitting diode (LED) light source without modulation, and the dots represent modulated and demodulated data points for a Hadamard mask (m=6) having 64 elements.
Figure 5B:
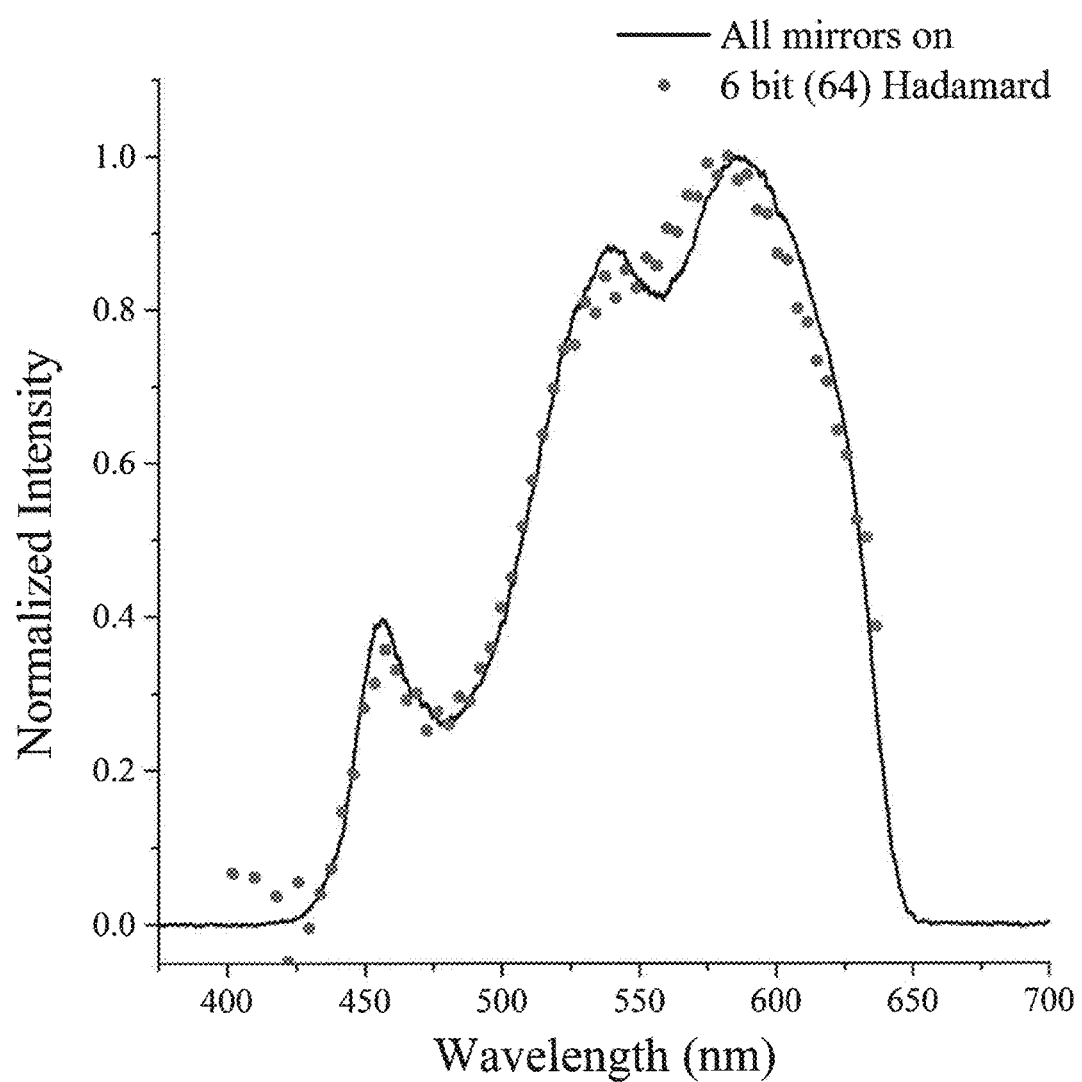

Modulation of the spectrometer's tungsten-halogen light source (Fiberlight, 3100, Boxborough, Mass.) was carried out using the fibre-coupled grating as the dispersive element. FIGS. 5A and 5B show the results, wherein the line in each plot represents the emission spectrum without modulation (i.e., all the mirrors are on, so that the DMA acts as a conventional mirror).

Figure 6A:
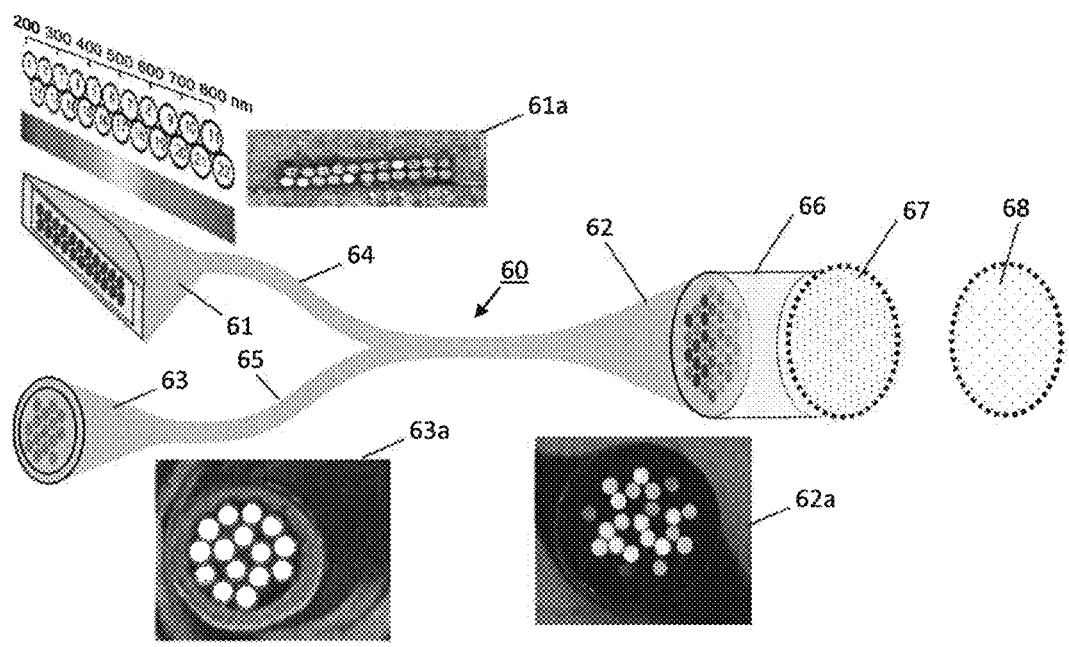
FIG. 6A is a schematic drawing of a bifurcated fibre probe according to one embodiment.
Figure 7:
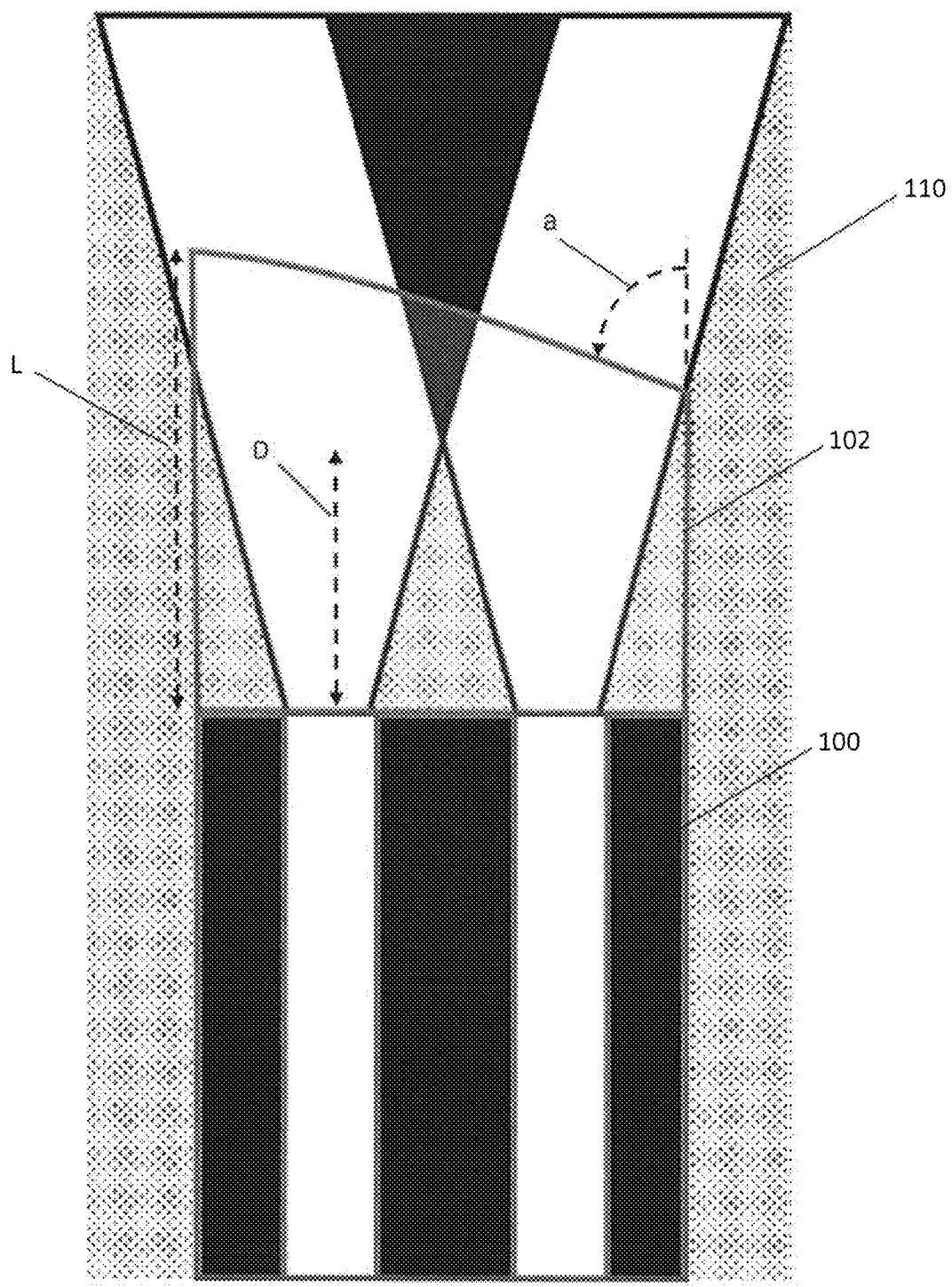
FIG. 7 is a schematic drawing showing a bevelled window coupled to a fibre probe to maximise acceptance cone overlap and reduce back reflections.

Since the modulated light that is reflected by the DMA is rectangular in shape, it cannot be efficiently coupled into the circular end of a conventional fibre probe or fibre bundle. Therefore, to maximise overlap and increase collection of the excitation light, a bifurcated probe was designed and built where the ends of the excitation fibres were arranged in a rectangular pattern as shown in FIG. 6A. The bifurcated probe 60 in FIG. 6A was designed to be sensitive to EEM fluorescence from both strongly and weakly absorbing samples, indicated schematically at 67 and 68, respectively. In the embodiment of FIG. 6A, 61, 62, and 63 denote the excitation, probe, and emission fibre ends, respectively, with corresponding inset photos 61a, 62a, and 63a. Excitation and emission fibre bundles 64, 65, respectively, are combined into the bifurcated fibre bundle at the probe end 62. A quartz window 66 was attached to the probe end 62 so that the acceptance cones of the excitation and emission fibres overlap. FIG. 7 is a drawing showing a close-up of a probe end with such a window. This ensures that fluorescence occurring at the surface of the fibre probe is detected, since, in highly reabsorbing or scattering samples, primary and secondary absorption can lead to a large loss of information. To further improve performance, the window, which may be of, e.g., quartz, or UV-fused silica, etc., may be bevelled to maximise acceptance cone overlap and reduce back reflections.

In FIG. 7, a fibre probe end 100 is applied to a sample 110. A quartz window 102 of length L is disposed on the probe end. The distance for reabsorption (in the absence of the window) is shown as D. The window length L may be long enough to ensure overlap of all the acceptance cones, while the minimum length L may be the distance between the acceptance cone overlap and the fibre end, i.e., the minimum length L may be equal to D. The actual length depends on the numerical aperture of the probe and the distance between the fibres. For example, L may be up to several mm. The bevel angle a may be optimized to minimize or eliminate the back reflections, and this depends on the refractive index of the window and the amount of reabsorption of the sample. Since the refractive indices of the window and of the sample are likely to be different, a Fresnel reflection is produced, sending the excitation light back to the probe. This becomes more pronounced as the refractive index difference between the window and the sample increases, and the critical angle of reflection depends on this refractive index difference. Without the bevel excitation light will be reflected back to the collection fibres of the probe, which is undesirable. The bevel prevents the reflected light from entering the fibre probe. Thus, the angle of the bevel may be selected to minimize the amount of reflected light reentering the probe based on the refractive index difference. For example, in one embodiment a bevel of 81° was selected for use with a sample of lubrication oil.

To test the instrument and calibrate the wavelengths the DMA was used to sequentially select each of the 128 wavelength blocks and direct the light to a spectrometer. The total excitation bandwidth was about 200 nm. The rectangular probe provided coverage of substantially the entire excitation spectrum of a sample. The excitation spectrum was then obtained by modulating the DMA using the Walsh functions that constitute a $2^m$-element Hadamard matrix with m=3 to 8. The upper limit of m is given by the number of elements of the DMA or SLM. After inverse Hadamard transformation the reconstructed spectrum was obtained and overlaid as dots as shown in the examples of FIGS. 5A and 5B.

Figure 6B:
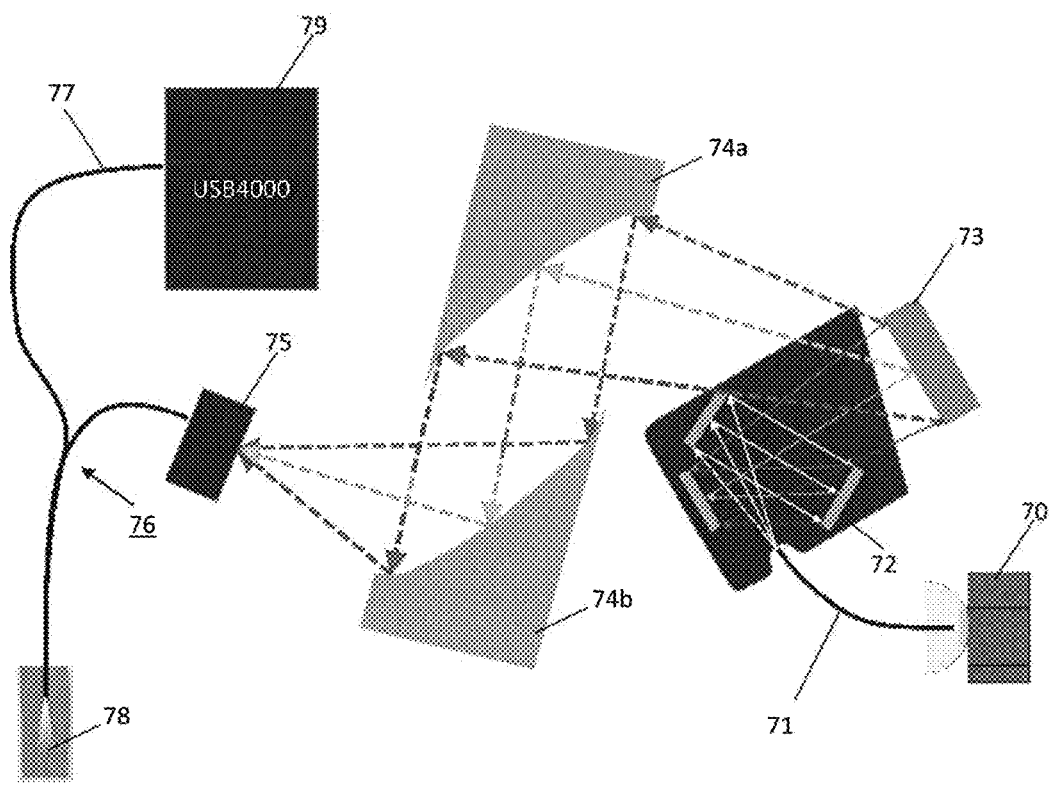
FIG. 6B is a schematic diagram of an EEM spectrometer according to one embodiment.

An embodiment of an EEM spectrometer is shown schematically in FIG. 6B. A light source 70 produces excitation light which is directed into a conduit 71, such as a fibre bundle. The fibre bundle directs the excitation light to a dispersion grating 72, and the light then reaches a DMA 73. In this embodiment, encoded light, shown by dashed lines, is directed through a pair of off-axis parabolic mirrors 74a, 74b, to the excitation end 75 of a bifurcated probe 76. The encoded light irradiates a sample 78, and fluorescence from the sample is directed through the emission end 77 of the probe 76 to a spectrometer 79.

Figure 8A:
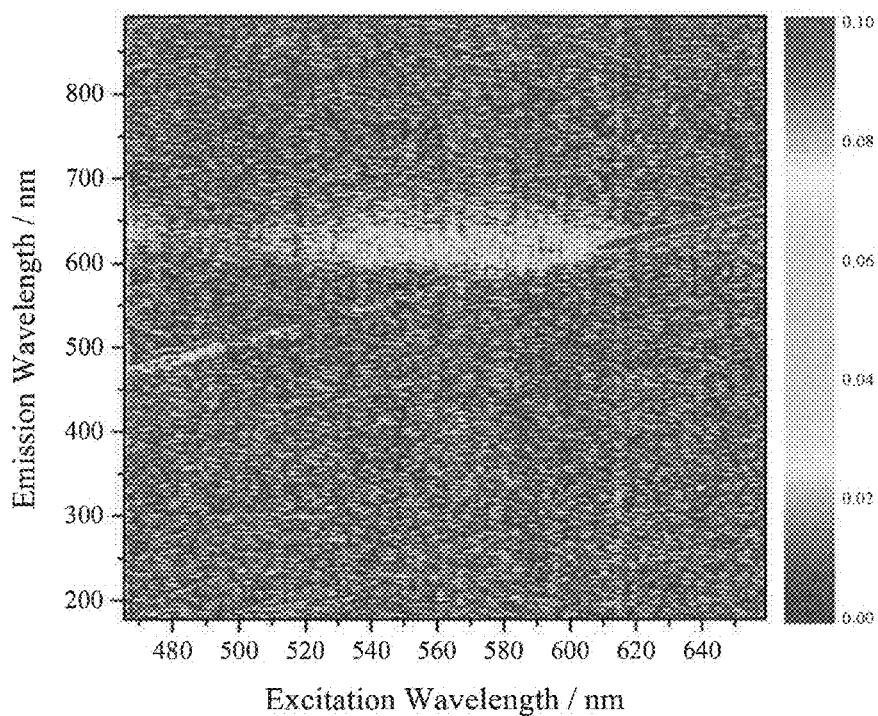
FIGS. 8A-8C show spectra of sulforhodamine 640, $1\times10^{-5}$ M in HPLC grade methanol using a DMA Hadamard EEM spectrometer (FIG. 8A, 128 pictures.
Figure 8B:
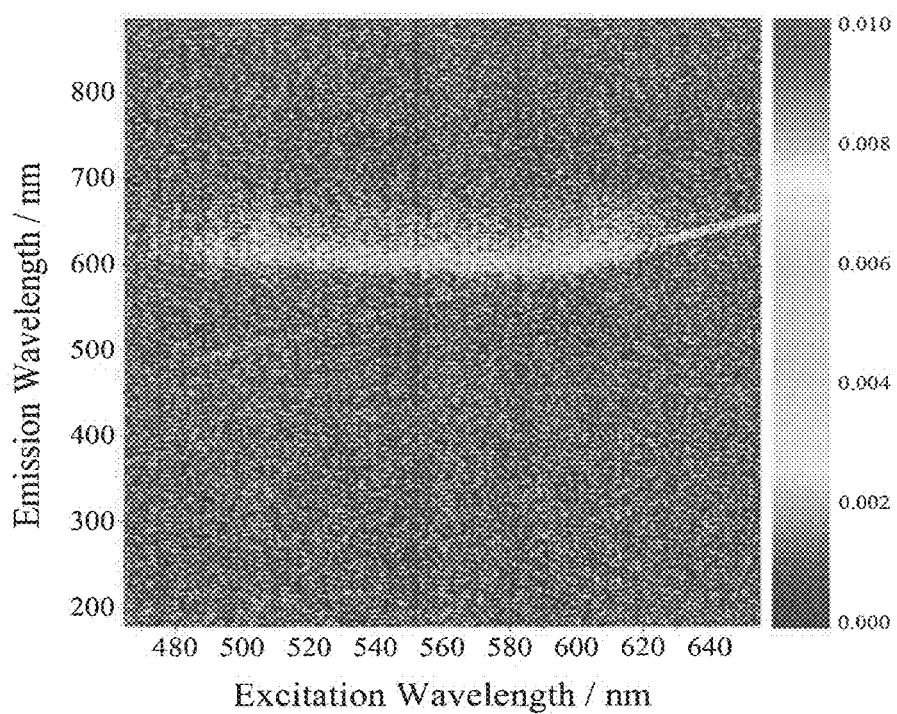
Figure 8C:
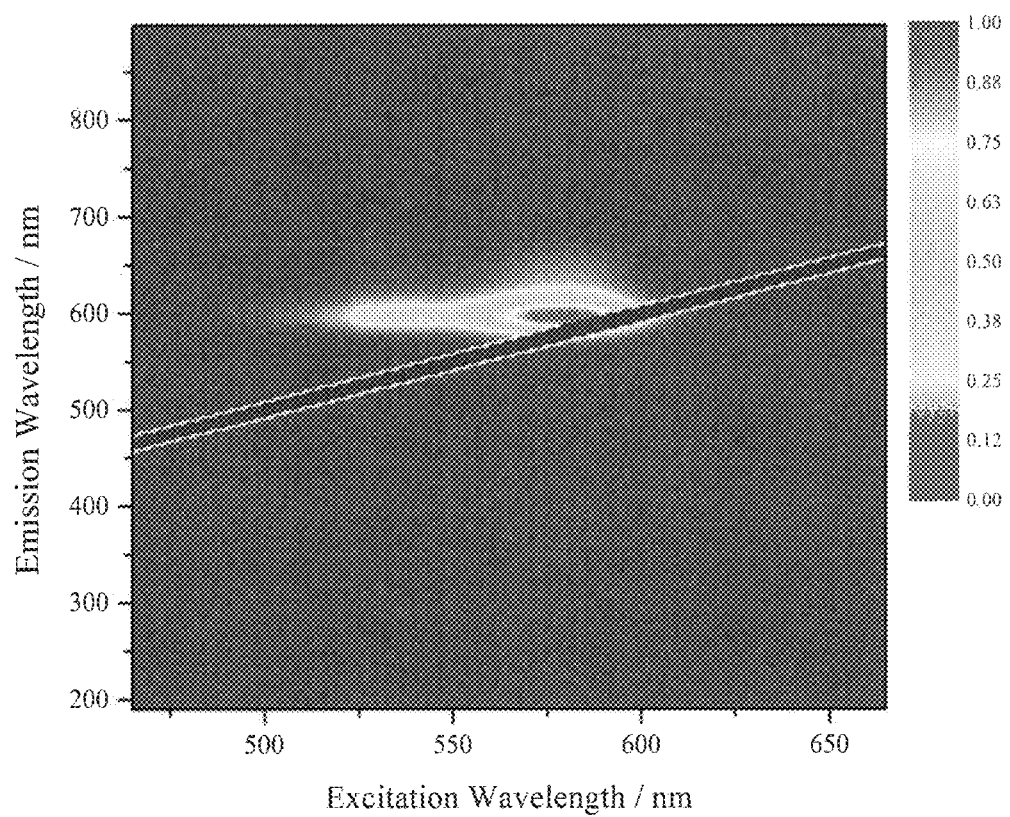

The probe was used to measure the excitation-emission matrix spectrum of the dye sulforhodamine 640. Sulforhodamine 640 was chosen for its absorption range, centred at 580 nm, which is near the centre of the excitation light source spectrum. A custom built code was written in MATLAB to control the DMA and spectrometer and to acquire the EEM fluorescence spectra. A second MATLAB code converted the modulated raw data into the EEM spectrum, as described above with reference to FIGS. 2-4. This code took about 19.8 s to run using a personal computer (Intel Core i7-2600 CPU @3.4 GHz). The EEM spectra obtained are shown in FIGS. 8A and 8B. For FIG. 8A, the Hadamard matrix had an order of m=7, i.e., it used 128 elements with an integration time of 2 s each, giving a total data acquisition time of 4 min 10 s. For FIG. 8B, an m=8 Hadamard matrix used 256 elements with an integration time of 2.5 s each, giving a total data acquisition time of 10 min 25 s. For comparison, FIG. 8C shows the EEM spectrum of sulforhodamine 640 ($1\times10^{-5}$ M) in HPLC grade methanol, obtained using a Varian Cary Eclipse spectrometer (slit size was 5 nm, PMT was set to 680 V, scan rate of 2400 nm/min, and auto filters on, total scan duration of 85 min). Thus, the DMA Hadamard EEM spectra were recorded in a fraction of the time required by the Varian Cary Eclipse spectrometer.

In another experiment the Hadamard EEM spectra were enhanced by replacing the pinhole in the reconfigured Ocean Optics USB-2000 (i.e., the dispersion element) with an array comprising 11 multimode fibres (core 400 μm, cladding 440 μm), which were arranged in a single row. This increased the amount of light entering the sample and consequently the fluorescence intensity, while maintaining a good dispersive resolution on the DMA. A translation stage was added between the dispersion grating and the DMA so that the dispersed light could be optimally focused on the DMA.

Figure 9A:
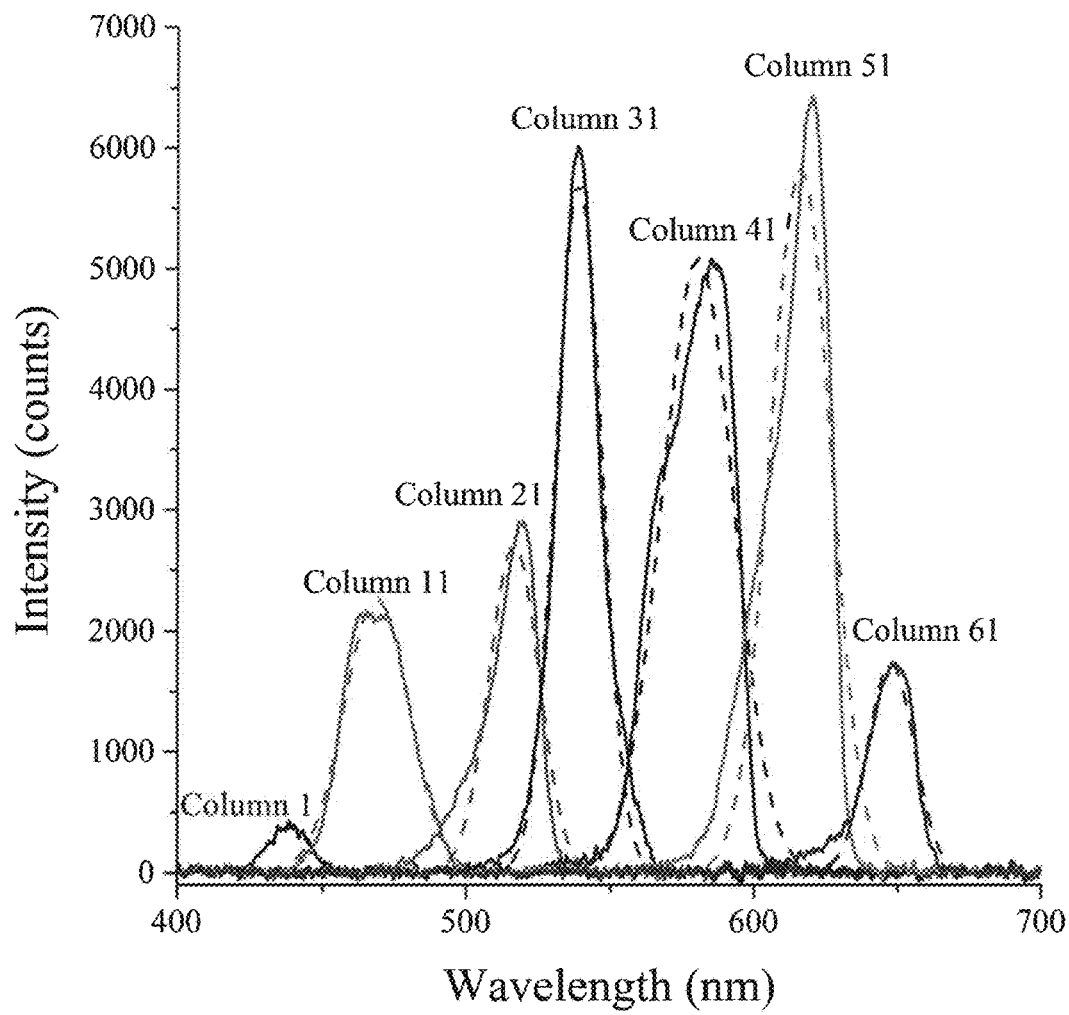
FIG. 9A shows spectra of columns of mirrors on a DMA obtained by sequentially the mirrors on in a column-by-column line scan.
Figure 9B:
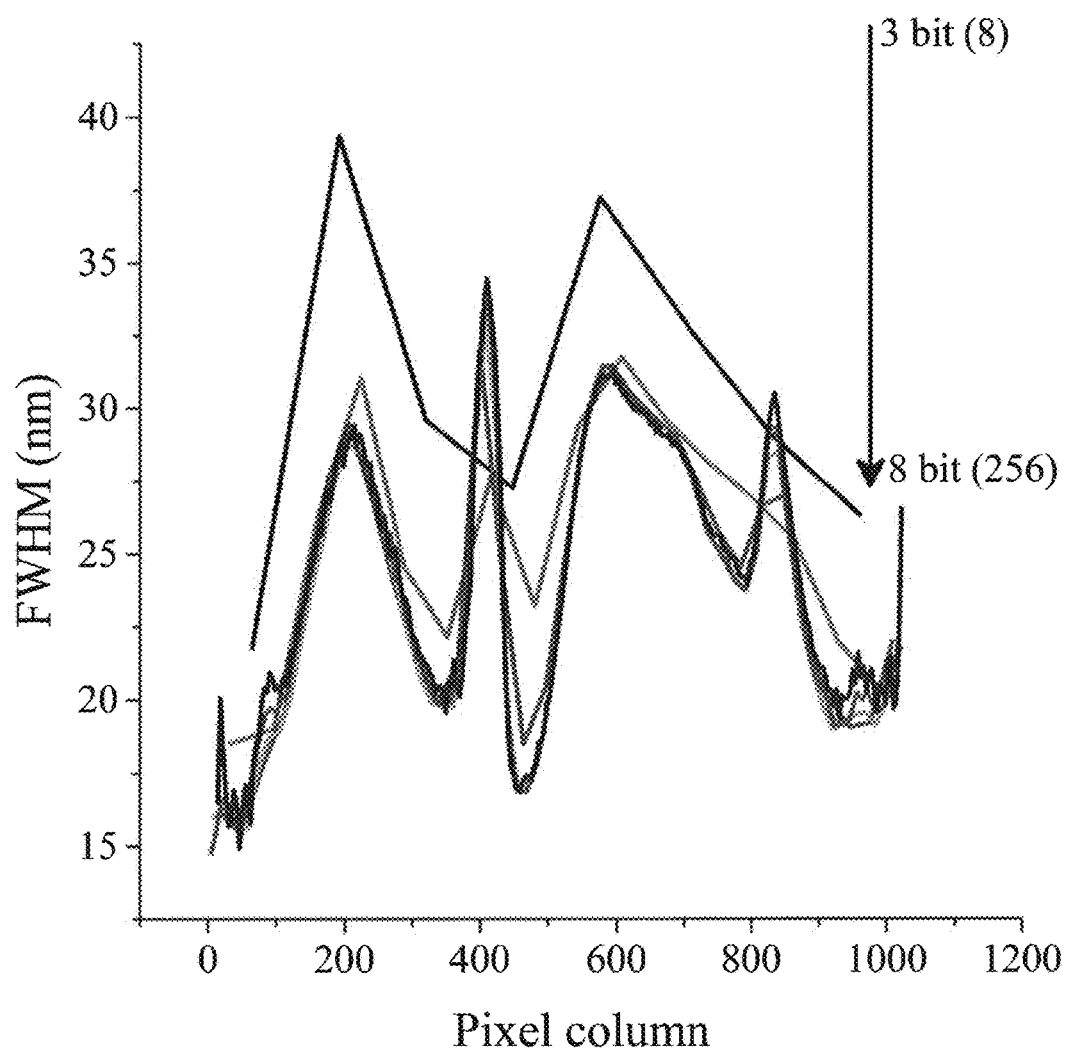
FIG. 9B is a plot of the full width half maximum (FWHM) obtained from the spectra of FIG. 9A.
Figure 9C:
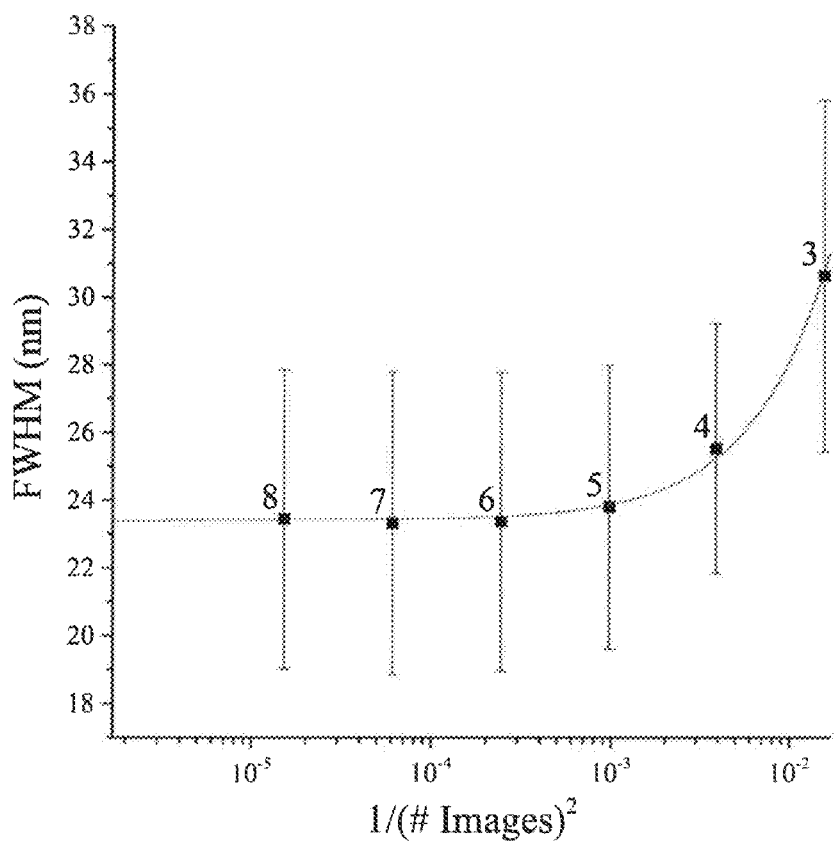
FIG. 9C is a plot of the average FWHM over the columns.
Figure 9D:
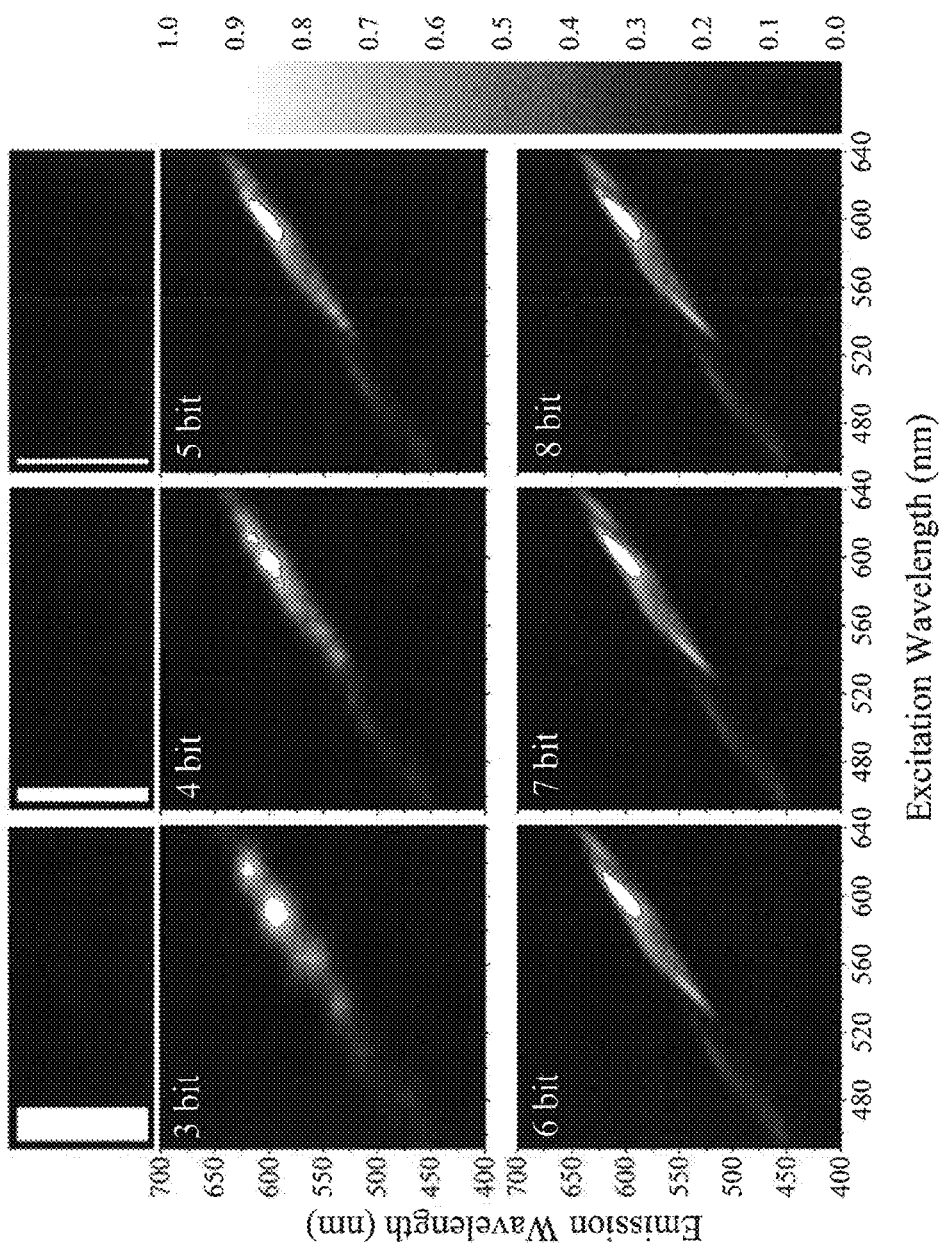
FIG. 9D shows the calibration spectra obtained by plotting the emission wavelength against the excitation wavelength.

Spectra of each column of mirrors on the DMA may be obtained by sequentially turning the mirrors on in a column-by-column conventional line scan of the DMA (see, e.g., FIG. 9A). The excitation wavelengths may be calculated by determining the central wavelength of the Gaussian fit for each column. This fit also gives the full width half maximum (FWHM), which allows calculation of the dispersive resolution on the DMA for each column (see FIG. 9B). FIG. 9C, which shows the average FWHM over all columns, shows that the average resolution is limited by the DMA and converges to 23 nm. Consequently, for this embodiment, there is no additional resolution advantage in increasing the number of excitation channels to over 6-bit (64 images), i.e., a 6×6 Hadamard matrix provides optimal resolution at the maximal data acquisition rate. FIG. 9D shows the calibration spectra obtained from this embodiment. The excitation wavelength axis obtained from the Gaussian fits give a matching linear response when plotted against the emission wavelength—500 nm excitation matches 500 nm emission—as expected when detecting scattered light from a white surface.

The excitation range of this embodiment was between 440-660 nm, and the excitation maximum was around 590 nm. Accordingly, sulforhodamine 640 was selected as a suitable compound to test this embodiment. As a reference, spectrum of sulforhodamine 640 $5\times10^{-5}$ M in ethanol is shown in FIG. 10C as obtained using the standard EEM scanning technique (Varian Cary Eclipse).

Figure 10A:
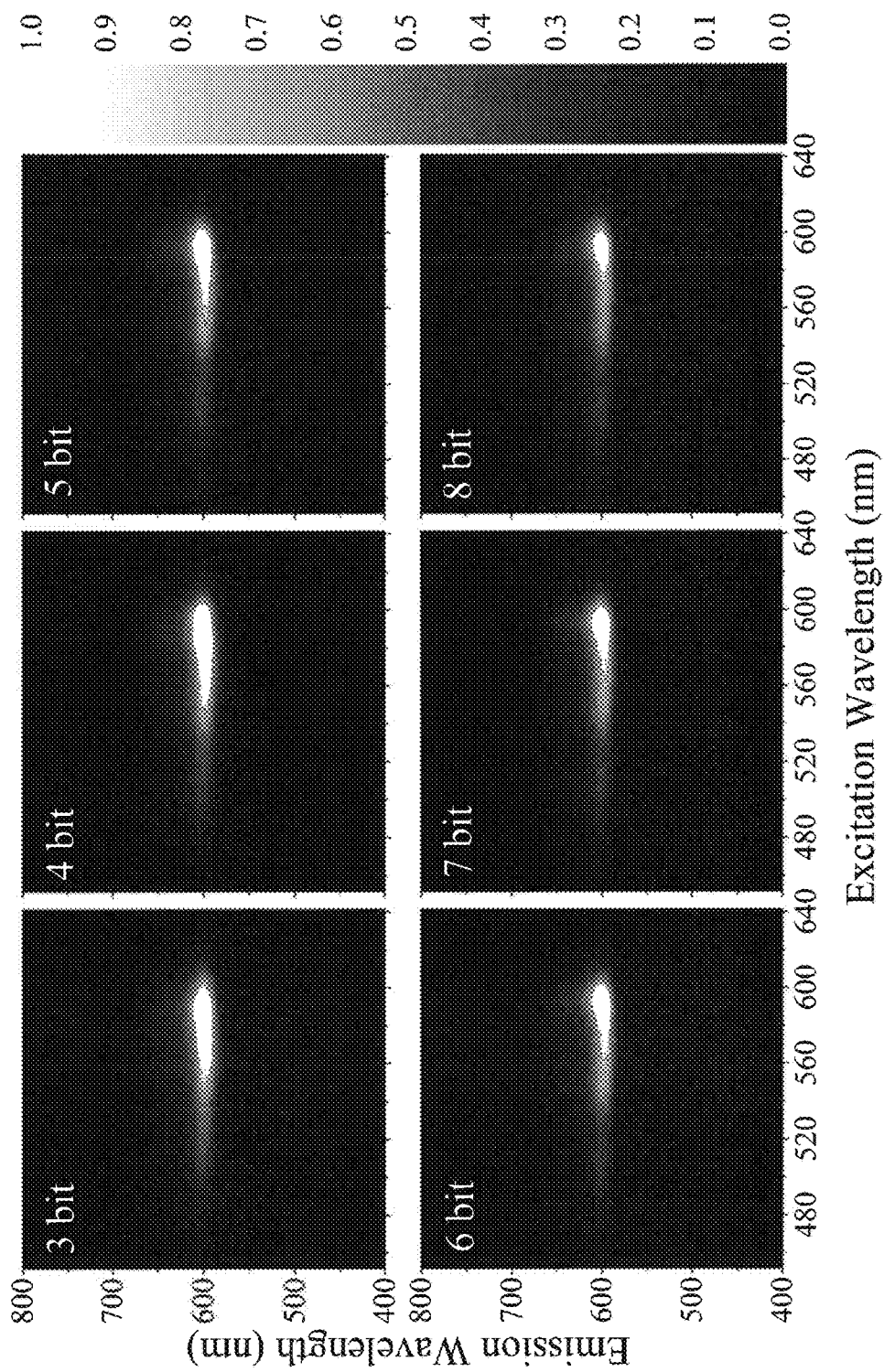
FIGS. 10A-10C show spectra of sulforhodmine 640, $5\times10^{-5}$ M in absolute ethanol, obtained using a DMA Hadamard EEM spectrometer (integration time 900 according to embodiments described herein (FIGS. 10A and 10B), and using a Varian Cary Eclipse spectrometer (FIG. 10C)

Using this embodiment, the Hadamard fluorescence spectra of the same solution of sulforhodamine 640, shown in FIG. 10A were obtained using an integration time of 900 ms for each of the $2^m$ exposures (m=3-8). The acquisition time for each EEM spectrum is the integration time multiplied by $2^m$ (number of images). Therefore, it takes 7.2 s for a 3-bit modulation, and 57.6 s for a 6-bit modulation. As can be observed, the Hadamard spectra (FIG. 10A) match those of the Varian spectrometer (FIG. 10C) while taking only a fraction of the time to complete (i.e., 1 minute vs 2 hours).

Figure 10B:
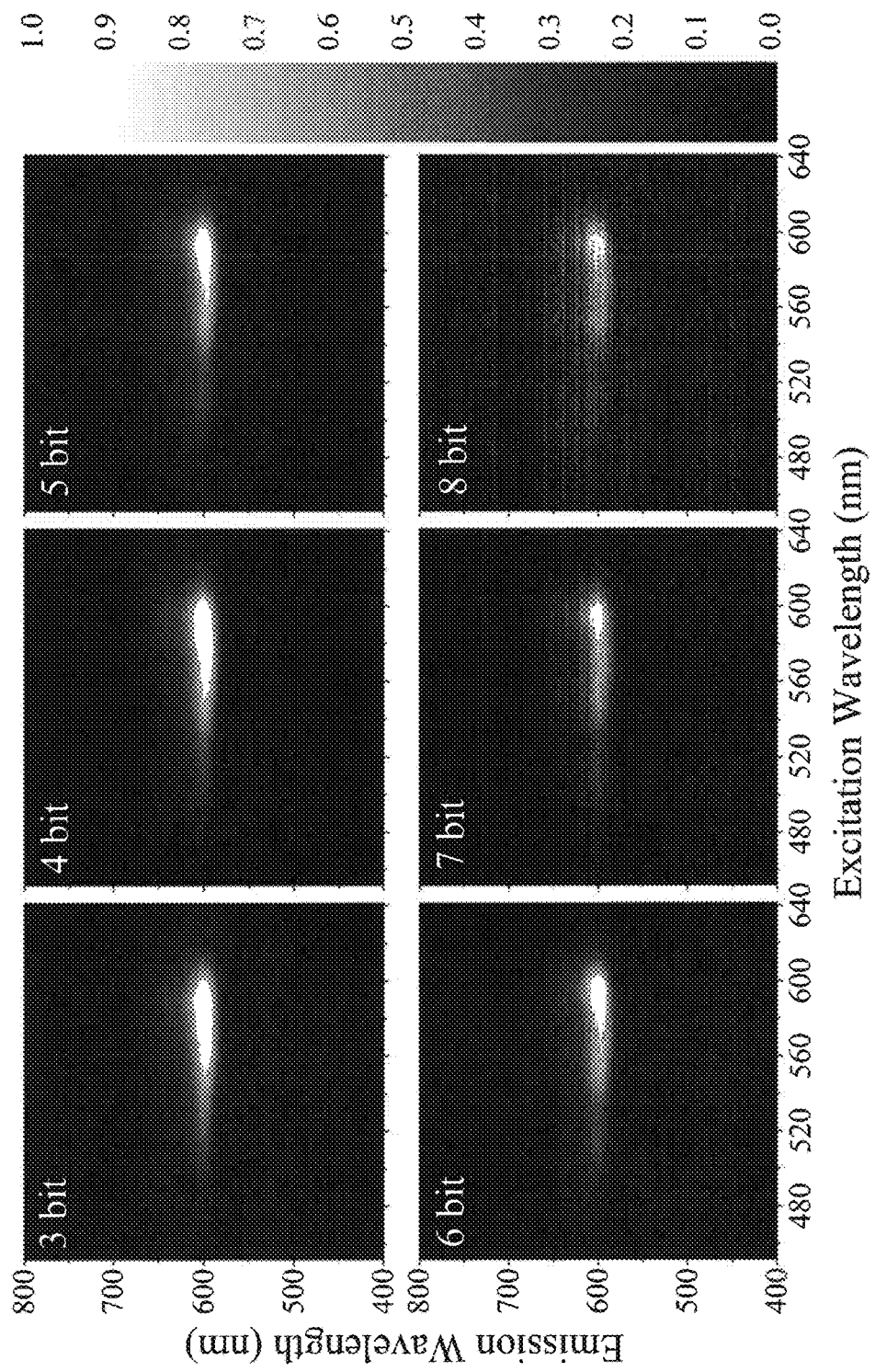
Figure 10C:
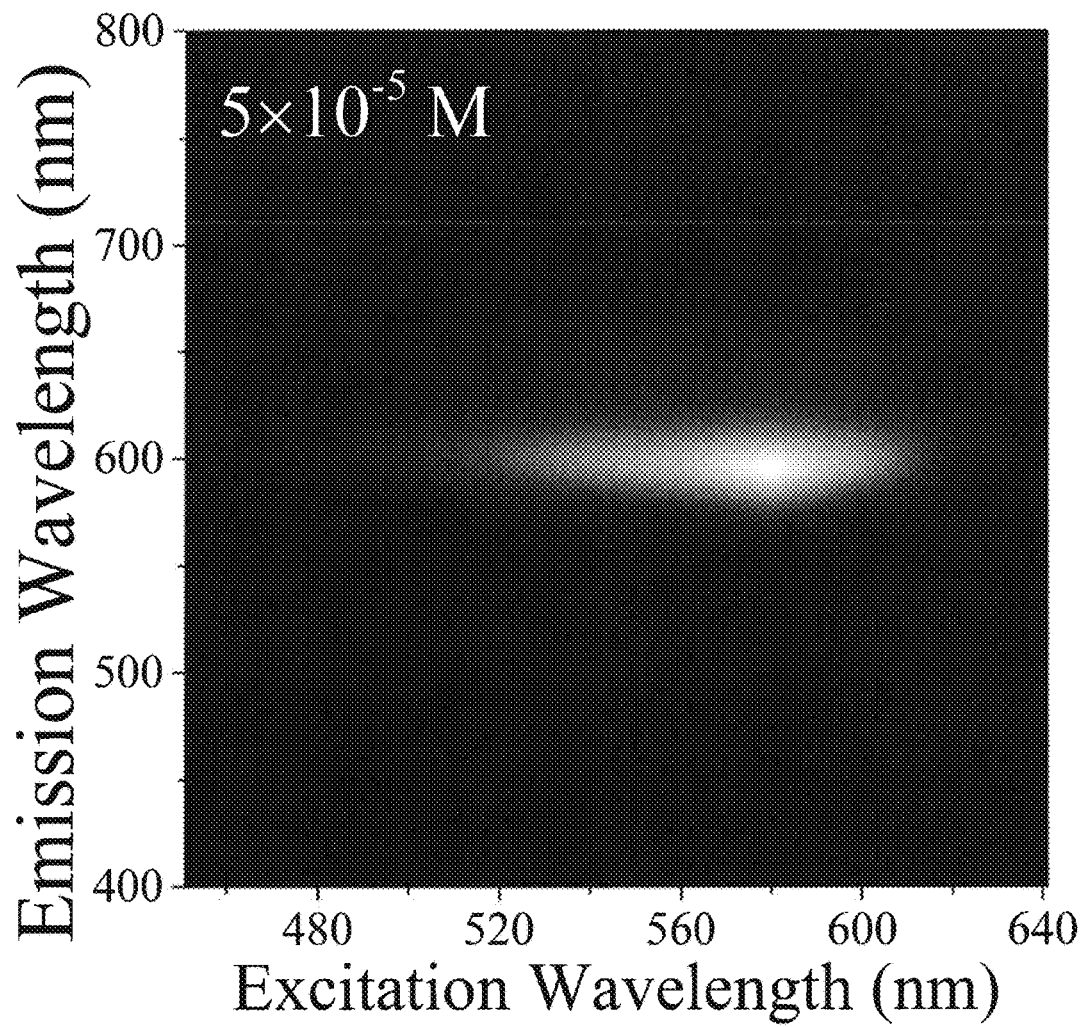

To better compare and show the advantages of the Hadamard embodiments described herein, conventional line scans using the same bit rates (3-8 bit) and sulforhodamine 640 solution were obtained, and are shown in FIG. 10B. These spectra were acquired with the DMA based embodiment described above, but the columns of mirrors were turned on sequentially—the same way that the calibration scans were performed. This simulated a conventional scanning light source, similar to the technique employed by the Varian spectrometer. As before, the total data acquisition time per EEM is 900 ms×$2^m$.

Figure 11:
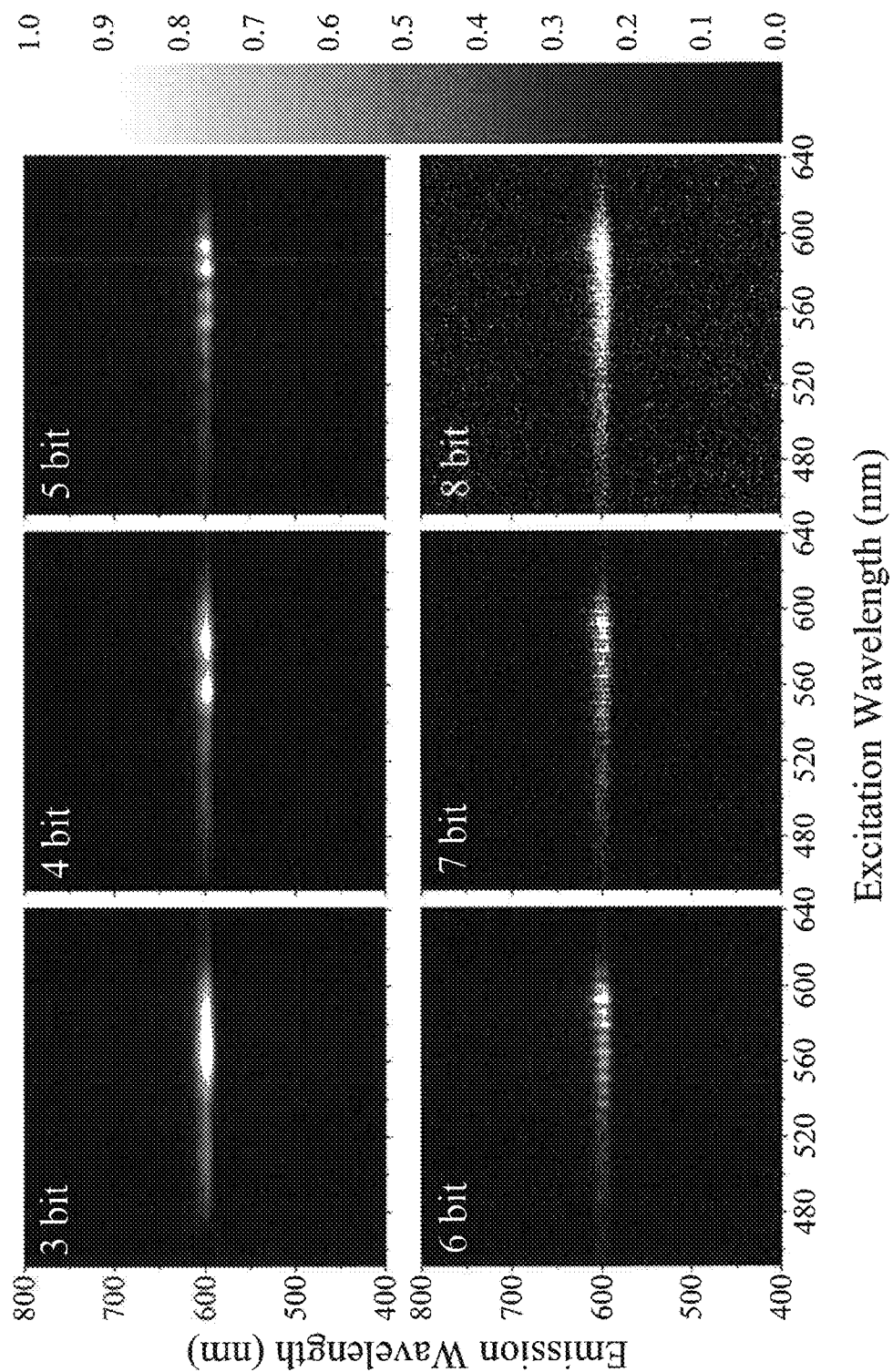
FIG. 11 shows spectra of sulforhodmine 640, $5\times10^{-5}$ M in absolute ethanol obtained using a DMA Hadamard EEM spectrometer with an integration time of 90 ms, according to an embodiment described herein.

To further highlight the advantages of Hadamard-based embodiments, further spectra (3-8 bit) were collected for sulforhodamine 640, with the integration time reduced to 90 ms (FIG. 11). With this integration time only 5.76 s were required to obtain a 6-bit (64 image) spectrum. This is comparably fast and highlights the technique's ability for real-time EEM measuring of samples. However, using such short integration times with a conventional line scan EEM produces a signal that is too low and too noisy to interpret (data not shown).

Spectra obtained by sequentially switching each of the columns "on", i.e., by scanning the excitation source in a conventional line scan match those of FIGS. 8A, 8B, and 9D, respectively—but have significantly lower intensity and higher noise (accordingly, the spectra are not presented). This is due to the difference in the amount of light directed into the sample for each method. For the line scan method, a higher bit number corresponds to a smaller column width, and a smaller fraction of light reflected. Due to the nature of the Walsh functions, in the Hadamard sequence—irrespective of the bit rate—exactly half of the total light reaching the DMA is reflected per image.

EXAMPLE 2

Further Embodiments

It is expected that performance of the embodiment described above may be improved when using a more powerful light source or pulsed light source to obtain a stronger fluorescence signal. A more sensitive array spectrometer based, e.g., on a thinned CCD array chip will also increase the signal-to-noise ratio. Refinements to the MATLAB (or other) code will allow EEM spectral acquisition and demodulation of the signal to be done simultaneously and continuously. Such optimization is expected to allow monitoring EEM spectra in real-time. Further, excitation wavelengths may be extended into UV for use in further applications. Also contemplated is an embodiment with simultaneous Hadamard-encoding of the excitation and emission light using a single photo multiplier tube (PMT) detector. PMTs are much faster and more sensitive than CCD arrays and this is expected to allow to sensing analytes in situ and in real-time.

The EEM spectrometer may be simplified and made more compact by using multiple (e.g., 8 or 16) different wavelength LEDs or lasers to cover targeted regions of the UV-NIR-IR spectrum. In such an embodiment, each light source is separately modulated by switching the sources on and off, according to the Walsh functions that constitute a Hadamard mask. Fluorescence may be collected using a bifurcated fibre bundle and detected using a spectrometer (e.g., a compact Ocean Optics or Avantes UV-NIR spectrometer).

This embodiment may not have as high a spectral resolution as the DMA Hadamard spectrometer, but for measurements of known analytes it may provide the required information. In addition, UV LEDs and lasers permit measurements in the UV region of the spectrum, which are currently complicated by the reduced reflectivity of the commercial micromirrors in this range. Embodiments may employ newly-available intense LED light sources at wavelengths below 280 nm for this purpose.

Figure 12A:
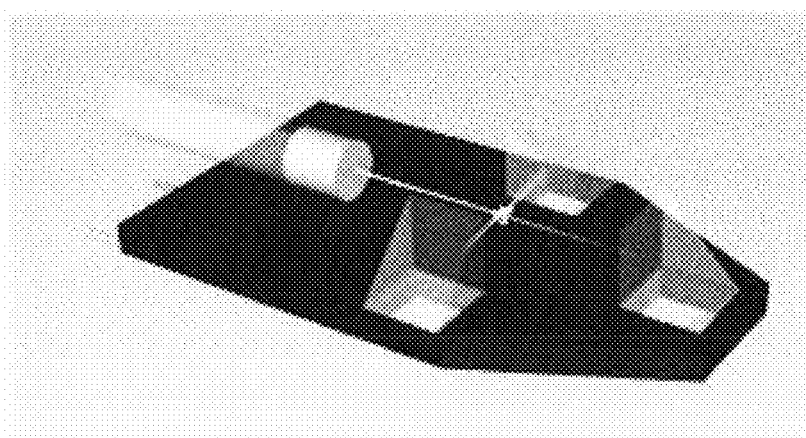
FIGS. 12A and 12B are diagrams of a fibre probe with a fibre bundle and quartz spacer, according to one embodiment.
Figure 12B:
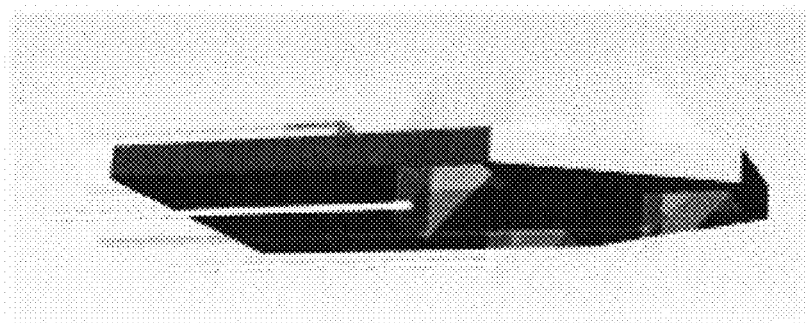

Alternatively or in addition to the above-mentioned fluorescence, the system may also be used to monitor phosphorescence, Raman signal, stimulated-Raman signal, resonance-enhanced Raman signal, and surface-enhanced Raman signal. Also, in addition to light emission, absorption and transmission may also be monitored by reconfiguring the fibre probe for transmission measurements. FIGS. 12A and 12B show an example of such a probe. Modulated light emitted from a fibre bundle (e.g., similar to that shown in FIG. 6) passes through the sample and is then collected at a prism P to be recoupled into the fibre bundle and detected by a PMT detector. The fibre bundle may have, e.g., 16-32 interleaved emission and collection fibres. Depending on the analyte, the sample's absorption spectrum may thereby be obtained after an inverse Hadamard transform of the signal at the detector. Sudden changes in transmission at all wavelengths indicates the presence of particulates in the probe volume. Scattering by particulates may be detected using two or more additional probes with photodetectors at each fibre. Accordingly, the spectrometer is useful for measuring the concentration of solid particles in solution.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

The invention claimed is:

1. An excitation emission matrix (EEM) spectrometer, comprising:
   at least one excitation light source that produces an excitation light spectrum;
   a multiplexer that:
      divides the excitation light spectrum into a plurality of discrete excitation wavelength ranges;
      selects three or more discrete excitation wavelength ranges from the plurality of discrete excitation wavelength ranges while rejecting remaining discrete excitation wavelength ranges; and
      encodes the selected three or more discrete excitation wavelength ranges according to a binary function;
   a conduit that conducts the encoded three or more discrete excitation wavelength ranges to a sample;
   a conduit that conducts an encoded emitted light from the sample;
   a spectrometer that detects the encoded emitted light and resolves a spectrum of the encoded emitted light; and
   a demultiplexer that decodes the encoded three or more discrete excitation wavelength ranges in the emitted light spectrum according to the binary function to produce an output EEM spectrum.

2. The EEM spectrometer of claim 1, wherein the emitted light is produced by at least one of luminescence, scattering, and transmission.

3. The EEM spectrometer of claim 2, wherein the luminescence comprises fluorescence, and/or the scattering comprises Raman scattering.

4. The EEM spectrometer of claim 1, wherein the multiplexer and the demultiplexer comprise FDM or OFDM.

5. The EEM spectrometer of claim 1, wherein both the selected three or more discrete excitation wavelength ranges and the emitted light are encoded using a DMA or a SLM.

6. The EEM spectrometer of claim 5, wherein the same DMA or SLM is used to encode the selected three or more discrete excitation wavelength ranges and the emitted light.

7. The EEM spectrometer of claim 1, wherein the selected three or more discrete excitation wavelength ranges are encoded by a DMA or SLM and the emitted light is recorded by a photoarray detector.

8. The EEM spectrometer of claim 1, wherein the selected three or more discrete excitation wavelength ranges are encoded using a Walsh function.

9. The EEM spectrometer of claim 1, wherein the selected three or more discrete excitation wavelength ranges are encoded using a Walsh function and the emitted light is decoded using an inverse Hadamard transformation.

10. The EEM spectrometer of claim 1, wherein the conduit that conducts the encoded selected three or more discrete excitation wavelength ranges the sample and the conduit that conducts encoded emitted light from the sample comprise a bifurcated fibre probe.

11. The EEM spectrometer of claim 1, further comprising a bifurcated fibre probe.

12. The EEM spectrometer of claim 11, wherein the bifurcated fibre probe comprises;
   an excitation end from which a first set of optical fibres receives excitation light;
   an emission end from which a second set of optical fibres emit emitted light; and
   a probe end from which the selected three or more discrete excitation wavelength ranges are outputted from the first set of optical fibres and the emitted light is received from a sample by the second set of optical fibres;
   wherein the probe comprises a bevelled window that reduces back reflections.

13. The EEM spectrometer of claim 1, comprising a display device that that displays the output EEM spectrum.

14. An excitation emission matrix (EEM) spectroscopy method, comprising:
using a multiplexer to:
divide an excitation light spectrum into a plurality of discrete excitation wavelength ranges;
select three or more discrete excitation wavelength ranges from the plurality of discrete excitation wavelength ranges while rejecting remaining discrete excitation wavelength ranges; and
encode the selected three or more discrete excitation wavelength ranges according to a binary function;
conducting the encoded three or more discrete excitation wavelength ranges to a sample;
conducting encoded emitted light from the sample; and
detecting and resolving a spectrum of the encoded emitted light; and
using a demultiplexer to decode the encoded three or more discrete excitation wavelength ranges in the emitted light spectrum according to the binary function and produce an output EEM spectrum.

15. The method of claim 14, comprising multiplexing and demultiplexing using FDM or OFDM.

16. The method of claim 14, comprising encoding the selected three or more discrete excitation wavelength ranges using a DMA or SLM.

17. The method of claim 16, comprising encoding the selected three or more discrete excitation wavelength ranges and decoding the emitted light using the same DMA or SLM.

18. The method of claim 14, comprising encoding the selected three or more discrete excitation wavelength ranges using a DMA or SLM and recording the emitted light using a photoarray detector.

19. The method of claim 14, comprising encoding the selected three or more discrete excitation wavelength ranges using Walsh functions.

20. The method of claim 14, comprising encoding the selected three or more discrete excitation wavelength ranges using Walsh functions and decoding the emitted light using an inverse Hadamard transformation.

21. The method claim 14, comprising using a bifurcated probe to conduct the encoded selected three or more discrete excitation wavelength ranges to the sample and to conduct encoded emitted light from the sample.

22. The method of claim 21, comprising using a bifurcated fibre probe wherein the probe comprises a bevelled window that reduces back reflections.

23. The method of claim 14, comprising displaying the output EEM spectrum.

* * * * *

UNITED STATES PATENT AND TRADEMARK OFFICE
CERTIFICATE OF CORRECTION

PATENT NO. : 10,481,092 B2
APPLICATION NO. : 15/216296
DATED : November 19, 2019
INVENTOR(S) : Hans-Peter Loock et al.

Page 1 of 1

It is certified that error appears in the above-identified patent and that said Letters Patent is hereby corrected as shown below:

Column 14, Claim 10, Line 51: replace "discrete excitation wavelength ranges the sample and the" with -- discrete excitation wavelength ranges to the sample and the --

Signed and Sealed this
Third Day of March, 2020

Andrei Iancu
*Director of the United States Patent and Trademark Office*